(12) United States Patent
Champion et al.

(10) Patent No.: US 12,371,680 B2
(45) Date of Patent: *Jul. 29, 2025

(54) TERMINAL DEOXYNUCLEOTIDYL TRANSFERASE VARIANTS AND USES THEREOF

(71) Applicant: DNA Script, Le Kremlin-Bicêtre (FR)

(72) Inventors: Elise Champion, Paris (FR); Jérôme Loc'h, Le Kremlin-Bicêtre (FR); Mikhael Soskine, Franconville (FR); Elodie Sune, Le Kremlin-Bicêtre (FR)

(73) Assignee: DNA Script SAS, Le Kremlin-Bicêtre (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/504,010

(22) Filed: Nov. 7, 2023

(65) Prior Publication Data

US 2024/0093165 A1     Mar. 21, 2024

Related U.S. Application Data

(63) Continuation of application No. 17/293,017, filed as application No. PCT/EP2019/081099 on Nov. 13, 2019, now Pat. No. 11,859,217.

(30) Foreign Application Priority Data

Nov. 14, 2018  (EP) .................................... 18206298
May 28, 2019   (EP) .................................... 19305677
Sep. 5, 2019   (EP) .................................... 19195662

(51) Int. Cl.
*C12N 9/12*       (2006.01)

(52) U.S. Cl.
CPC .... *C12N 9/1264* (2013.01); *C12Y 207/07031* (2013.01)

(58) Field of Classification Search
CPC .................................................... C12N 9/1264
See application file for complete search history.

(56) References Cited

U.S. PATENT DOCUMENTS

| 5,436,143 A | 7/1995 | Hyman |
| 5,739,386 A | 4/1998 | Holmes |

(Continued)

FOREIGN PATENT DOCUMENTS

| CA | 3024184 A1 | 12/2017 |
| CN | 105264085 A | 1/2016 |

(Continued)

OTHER PUBLICATIONS

Q5EB91_RAT. UnitProtKB/TrEMBL. May 23, 2018.*

(Continued)

*Primary Examiner* — Yong D Pak
(74) *Attorney, Agent, or Firm* — MORRISON & FOERSTER LLP

(57) ABSTRACT

The present invention is directed to terminal deoxynucleotidyltransferase (TdT) variants that (i) comprise an amino acid sequence that is at least a specified percent identical to an indicated SEQ ID NOs and have at least one substitution at Q455 or at least Q455 plus at least one further substitution at G186, S248, T331, Q390, K394 or H466 (where positions are with respect to SEQ ID NO 1 and functionally equivalent positions in indicated SEQ ID NOs), (ii) are capable of template-free extension of a polynucleotide, and (iii) exhibit enhanced stability or enhanced efficiency in incorporating 3'-0-blocked nucleoside triphosphates into a polynucleotide. The invention is also directed to the use of these TdT variants for synthesizing polynucleotides of any predetermined sequence.

8 Claims, 3 Drawing Sheets

Specification includes a Sequence Listing.

(56) References Cited

U.S. PATENT DOCUMENTS

| | | | |
|---|---|---|---|
| 5,763,594 | A | 6/1998 | Hiatt et al. |
| 5,808,045 | A | 9/1998 | Hiatt et al. |
| 7,057,026 | B2 | 6/2006 | Barnes et al. |
| 7,544,794 | B1 | 6/2009 | Benner |
| 8,808,988 | B2 | 8/2014 | Zhao et al. |
| 10,752,887 | B2 * | 8/2020 | Champion ............ C12N 9/1264 |
| 10,760,063 | B2 | 9/2020 | Efcavitch et al. |
| 10,774,316 | B2 | 9/2020 | Efcavitch et al. |
| 11,390,858 | B2 | 7/2022 | Tubbs et al. |
| 11,859,217 | B2 | 1/2024 | Champion et al. |
| 2005/0037991 | A1 | 2/2005 | Bodepudi et al. |
| 2022/0112534 | A1 | 4/2022 | Chen et al. |

FOREIGN PATENT DOCUMENTS

| | | |
|---|---|---|
| CN | 107567501 A | 1/2018 |
| FR | 3052462 A1 | 12/2017 |
| WO | 91/06678 A1 | 5/1991 |
| WO | 2004/005667 A1 | 1/2004 |
| WO | 2015/159023 A1 | 10/2015 |
| WO | 2016/064880 A1 | 4/2016 |
| WO | 2017/216472 A2 | 12/2017 |
| WO | WO-2018215803 A1 * 11/2018 ............. C12N 15/10 |
| WO | 2020/099451 A1 | 5/2020 |

OTHER PUBLICATIONS

Becker, A. et al. (1967) "The Enzymatic Cleavage of Phosphate Termini from Polynucleotides," J. Biol. Chem., 242(5):936-950.

Benatolila, L.A. et al. (1995). "The Two Isoforms of Mouse Terminal Deoxynucleotidyl Transferase Differ in Both the Ability to Add N Regions and Subcellular Localization," The EMBO Journal 14(17):4221-4229.

Boule, J-B. et al. (1998). "High-Level Expression of Murine Terminal Deoxynucleotidyl Transferase in *Escherichia coli* Grown at Low Temperature and Overexpressing argU tRNA", Molecular Biotechnology, 10:199-208.

Cameron, V. et al. (1977). "3'-Phosphatase Activity in T4 Polynucleotide Kinase", Biochemistry 16(23):5120-5126.

Canard, B. et al. (Nov. 21, 1995). "Catalytic Editing Properties of DNA Polymerases" Proc. Natl. Acad. Sci., 92:10859-10863.

Canard, B. et al. (Oct. 11, 1994). "DNA Polymerase Fluorescent Substrates with Reversible 3'-Tags" Gene 148(1):1-6.

Corpet, F. (Nov. 25, 1988). "Multiple Sequence Alignment with Hierarchical Clustering," Nucl. Acids Res. 16(22):10881-10890.

Delarue, M. et al. (Feb. 1, 2002). "Crystal Structures of a Template-Independent DNA Polymerase: Murine Terminal Deoxynucleolidyltransferase", The Embo Journal 21(3):427-439.

Ferrero, M. et al. (2000). "Chemoenzymalic Transformations in Nucleoside Chemistry" Monatshefte fur Chemie, 131:585-616.

Grantham, R. (1974). "Amino Acid Difference Formula to Help Explain Protein Evolution," Science 185(4154):862-864.

Jensen, M.A. et al. (Mar. 27, 2018. e-pub Mar. 13, 2018). "Template-Independent Enzymatic Oligonucleolide Synthesis (TiEOS): Its History, Prospects and Challenges" Biochemistry, 57:1821-1832.

Kodumal, S.J. et al. (2004). "Total Synthesis of Long DNA sequences: Synthesis of Acontiguous 32-kb Polyketide Synthase Gene Cluster", The National Academy of Sciences of the USA, 101(44):15573-15578.

Meng, Q. et al. (2006). "Design and Synthesis of a Photocleavable Fluorescent Nucleotide 3'-O-Allyl-dGTP-PC-Bodipy-FL-510 as Reversible Terminator for DNA Sequencing by Synthesis," J. Org. Chem. 71:3248-3252.

Metzker, M.L. et al. (Oct. 11, 1994). "Termination of DNA Synthesis by Novel 3'-Modifieddeoxyribonucleoside 5'-Triphosphates" Nucleic Acids Research, 22(20):4259-4267.

Rasolonjatovo, I. et al. (1999). "Development of a New DNA Sequencing Method: 3'-Ester Cleavage Catalyzed by Taq DNA Polymerase", Nucleosides & Nucleotides 18(4-5):1021-1022.

Schmitz, C. et al. (1999. E-pub. Nov. 6, 1999). "Solid-Phase Enzymatic Synthesis of Oligonucleotidest" Organic Lett. 1(11):1729-1731.

Stemmer, W.P. et al. (Oct. 16, 1995). "Single-step Assembly of a Gene and Entire Plasmid From Large Numbers of Oligodeoxyribonucleotides" Gene 164:49-53.

Taunton-Rigby, A. (1973). "Oligonucleotide Synthesis. III. Enzymically Removable Acyl Protecting Groups" J. Org. Chem. 38(5):977-985.

Uemura, A. et al. (1989). "Regioselective Deprotection of 3',5'-O-acylated Pyrimidine Nucleosides by Lipase and Esterase", Tetrahedron Lett. 30(29):3819-3820.

* cited by examiner

Fig. 2

Table 1

| SEQ ID NO | Supplemental Substitutions | | | | | | | | | | |
|---|---|---|---|---|---|---|---|---|---|---|---|
| | L181F/A/M/Y | M192R/Q | A237V | L260P/R/K | C302G/R | R336L/N | G413L/S | E418A/V | R454P/N/A/V | E457N/L/T/S/K | R480K/E/D |
| 1 | L181F/A/M/Y | M192R/Q | A237V | L260P/R/K | C302G/R | R336L/N | G413L/S | E418A/V | R454P/N/A/V | E457N/L/T/S/K | R480K/E/D |
| 3 | L52F/A/M/Y | M63R/Q | A108V | L131P/R/K | C173G/R | R207L/N | G284L/S | E289A/V | R325P/N/A/V | E328N/L/T/S/K | R351K/E/D |
| 4 | --- | M63R/Q | A110V | L131P/R/K | C173G/R | R207L/N | --- | --- | R324P/N/A/V | E327N/L/T/S/K | R353K/E/D |
| 5 | --- | M63R/Q | A110V | L131P/R/K | C173G/R | R207L/N | --- | E290A/V | R324P/N/A/V | E327N/L/T/S/K | R353K/E/D |
| 6 | --- | --- | A107V | --- | C172G/R | R206L/N | --- | --- | R320P/N/A/V | --- | --- |
| 7 | --- | M63R/Q | A110V | L131P/R/K | C173G/R | R207L/N | --- | E292A/V | R331P/N/A/V | E334N/L/T/S/K | --- |
| 8 | --- | M63R/Q | A110V | L131P/R/K | C173G/R | R207L/N | --- | --- | --- | --- | R354K/E/D |
| 9 | --- | --- | A111V | L132P/R/K | C174G/R | R208L/N | --- | --- | --- | E328N/L/T/S/K | --- |
| 10 | --- | M72R/Q | A110V | L131P/R/K | C173G/R | R207L/N | --- | E295A/V | R331P/N/A/V | E334N/L/T/S/K | --- |
| 11 | --- | M64R/Q | A111V | L132P/R/K | C174G/R | R208L/N | --- | --- | R325P/N/A/V | E328N/L/T/S/K | R355K/E/D |
| 12 | --- | M61R/Q | A108V | L129P/R/K | C171G/R | R205L/N | G284L/S | E293A/V | R323P/N/A/V | E326N/L/T/S/K | R352K/E/D |
| 13 | --- | M63R/Q | A110V | L131P/R/K | C173G/R | R207L/N | --- | E248A/V | R329P/N/A/V | E331N/L/T/S/K | --- |
| 14 | --- | --- | A110V | L131P/R/K | C174G/R | R207L/N | --- | --- | R325P/N/A/V | E328N/L/T/S/K | R354K/E/D |
| 15 | --- | M63R/Q | A110V | L131P/R/K | C182G/R | R216L/N | --- | E295A/V | R338P/N/A/V | E341N/L/T/S/K | --- |
| 16 | --- | M65R/Q | A113V | L134P/R/K | C176G/R | R210L/N | --- | E298A/V | R328P/N/A/V | E331N/L/T/S/K | --- |

Fig. 3

Table 2

| SEQ ID NO | Stability Substitutions | | | | | | | | | | | |
|---|---|---|---|---|---|---|---|---|---|---|---|---|
| | Q166E | D170R | C188R | L189D | S223R | G227E | S248A | S275E | Q278R | F322Y | V328M | M330V |
| 1 | Q166E | D170R | C188R | L189D | S223R | G227E | S248A | S275E | Q278R | F322Y | V328M | M330V |
| 3 | Q37E | D41R | C59R | L60D | S94R | G98E | S119A | S146E | Q149R | F193Y | V199M | M201V |
| 4 | -- | D41R | -- | -- | -- | -- | S119A | S146E | -- | F193Y | V199M | M201V |
| 5 | Q37E | D41R | C59R | L59D | -- | -- | S119A | S146E | -- | F193Y | V199M | M201V |
| 6 | -- | D40R | C58R | -- | -- | -- | S118A | -- | -- | F192Y | V198M | -- |
| 7 | Q37E | D41R | C59R | L60D | -- | -- | S119A | S146E | -- | F193Y | V199M | -- |
| 8 | -- | D41R | -- | -- | -- | -- | S119A | -- | -- | F193Y | V199M | M201V |
| 9 | Q37E | D42R | C60R | -- | -- | -- | S120A | -- | -- | -- | V200M | -- |
| 10 | -- | D41R | -- | L60D | -- | -- | S119A | S146E | -- | F193Y | V199M | M201V |
| 11 | -- | D42R | -- | -- | -- | -- | S120A | S147E | -- | F194Y | V200M | M202V |
| 12 | -- | D39R | -- | -- | S94R | -- | -- | S144E | -- | F191Y | -- | M199V |
| 13 | -- | D41R | C59R | -- | -- | -- | S119A | -- | -- | F193Y | V199M | M201V |
| 14 | -- | D41R | -- | L60D | S94R | -- | S119A | S146E | -- | F193Y | V199M | -- |
| 15 | Q37E | D41R | C59R | -- | -- | -- | S119A | -- | -- | F193Y | V199M | -- |
| 16 | -- | D44R | C62R | -- | -- | -- | S122A | -- | -- | F196Y | -- | -- |

TERMINAL DEOXYNUCLEOTIDYL TRANSFERASE VARIANTS AND USES THEREOF

CROSS REFERENCE TO RELATED APPLICATIONS

This application is a continuation of U.S. patent application Ser. No. 17/293,017, which adopts the international filing date of Nov. 13, 2019, which is a national stage application under 35 U.S.C. § 371 of International Application No. PCT/EP2019/081099, filed on Nov. 13, 2019, which claims the benefit of EP Application No. 18206298.4, filed on Nov. 14, 2018, EP Application No. 19195662.2, filed on Sep. 5, 2019, and EP Application No. 19305677.7, filed on May 28, 2019, the disclosure of which are hereby incorporated by reference in their entirety.

REFERENCE TO AN ELECTRONIC SEQUENCE LISTING

The content of the electronic sequence listing (283182000801 seqlist.xml; Size: 53,764 bytes; and Date of Creation: Nov. 3, 2023) is herein incorporated by reference in its entirety.

BACKGROUND

The use of highly purified inexpensive polynucleotides of predetermined sequences in a wide range of lengths has become central to a host of technologies, including genomic and diagnostic sequencing, multiplex nucleic acid amplification, therapeutic antibody development, synthetic biology, nucleic acid-based therapeutics, DNA origami, DNA-based data storage, and the like. Recently, interest has arisen in supplementing or replacing chemically-based synthesis methods by enzymatically-based methods using template-free polymerases, such as, terminal deoxynucleotidyl transferase (TdT), because of the proven efficiency of such enzymes and the benefit of mild non-toxic reaction conditions, e.g. Ybert et al, International patent publication WO2015/159023; Hiatt et al, U.S. Pat. No. 5,763,594; Jensen et al, Biochemistry, 57: 1821-1832 (2018); and the like. Most approaches in enzyme-based synthesis require the use of reversibly blocked nucleoside triphosphates in order to obtain a desired sequence in the polynucleotide product. Unfortunately, natural TdTs incorporate such modified nucleoside triphosphates with greatly reduced efficiency as compared to unmodified nucleoside triphosphates.

In view of the above, the field of template-free enzymatically-based polynucleotide synthesis would be advanced if new template-free polymerases, such as variant TdTs, were available that could incorporate reversibly blocked nucleoside triphosphates with greater efficiency.

SUMMARY OF THE INVENTION

The present invention is directed to terminal deoxynucleotidyl transferase (TdT) variants that display enhanced efficiency in incorporating reversibly blocked nucleoside triphosphates into a polynucleotide, and to their use in synthesizing polynucleotides of any predetermined sequence. Additionally, in some embodiments, TdT variants of the invention exhibit enhanced stability with respect to wildtype enzymes. In part the invention is based on the discovery that the efficiency of TdT-based nucleotide incorporation depends in part on the nucleotide sequence of the 3' end of the polynucleotide being extended; thus, the invention is in part an appreciation and recognition that TdT variants of the invention are capable of efficiently extending a polynucleotide independent of the nucleotide sequence of its 3' end.

In some embodiments, the invention is directed to a terminal deoxynucleotidyl transferase (TdT) variant comprising an amino acid sequence at least sixty percent identical to an amino acid sequence selected from SEQ ID NO: 3, 4, 5, 6, 7, 8, 9, 10, 11, 12, 13, 14, 15 of 16 with a substitution of glutamine at position 326 with respect to SEQ ID NOs 3, 8, 10 and 14, or glutamine at position 325 with respect to SEQ ID NO: 4 and 5. or glutamine at position 332 with respect to SEQ ID NO: 7 and 9, or glutamine at position 329 with respect to SEQ ID NO: 13 and 16, or glutamine at position 321 with respect to SEQ ID NO: 6, or glutamine at position 327 with respect to SEQ ID NO: 11, or glutamine at position 324 with respect to SEQ ID NO: 12, or glutamine at position 339 with respect to SEQ ID NO: 15. or glutamine at position 309 with respect to SEQ ID NO: 24 and 26, or glutamine at position 307 with respect to SEQ ID NO: 25, wherein the TdT variant (i) is capable of synthesizing a nucleic acid fragment without a template and (ii) is capable of incorporating a 3'-O-modified nucleotide onto a free 3'-hydroxyl of a nucleic acid fragment.

In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity: in some embodiments, the above percent identity value is at least 98 percent identity; in some embodiments, the above percent identity value is at least 99 percent identity. In some embodiments, the variant consists in a sequence selected from the group consisting in SEQ ID NO: 3, 4, 5, 6, 7, 8, 9, 10, 11, 12, 13, 14, 15, 16, 24, 25 or 26, with one or more of the disclosed amino acid substitutions. As used herein, the percent identity values used to compare a reference sequence to a variant sequence do not include the expressly specified amino acid positions containing substitutions of the variant sequence; that is, the percent identity relationship is between sequences of a reference protein and sequences of a variant protein outside of the expressly specified positions containing substitutions in the variant. Thus, for example, if the reference sequence and the variant sequence each comprised 100 amino acids and the variant sequence bad mutations at positions 25 and 81, then the percent identity would be in regard to sequences 1-24, 26-80 and 82-100.

In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In some embodiments, the above substitution for glutamine is selected from the group consisting of T, F, L and M; in other embodiments, the above substitution for glutamine is selected from the group consisting of T, F, L, M, I, V and Y. In some embodiments, said substitution is F. In some embodiments, the substitution of glutamine may be in combination with other mutations described herein, such as those at the lysine, histidine, alanine, tryptophan, glycine or glutamine below.

In some embodiments, the invention is directed to a terminal deoxynucleotidyl transferase (TdT) variant comprising an amino acid sequence at least sixty percent 60% identical to an amino acid sequence selected from SEQ ID NO: 3, 5, 6, 7, 8, 9, 10, 11, 12, 13, 14, 15 or 16 and comprising a substitution of lysine at position 265 with respect to SEQ ID NOs 3, 7, 8, 9, 10, 13 and 14, or lysine at position 263 with respect to SEQ ID NOs 6 and 12, or lysine at position 264 with respect to SEQ ID NO 5, or lysine at position 266 with respect to SEQ ID NO 11, or lysine at position 268 with respect to SEQ ID NO 16, or lysine at position 272 with respect to SEQ ID NO 15, wherein the TdT variant (i) is capable of synthesizing a nucleic acid fragment without a template and (ii) is capable of incorporating a 3'-O-modified nucleotide onto a free 3' hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate. In some embodiments, the amino acid substitution of lysine is selected from the group consisting of E, T, A and R. In some embodiments, said substitution is T. In some embodiments, the substitution of lysine may be in combination with other mutations described herein, such as those at the glutamine above, or the histidine, alanine, tryptophan, glycine or glutamine below.

In some embodiments, the invention is directed to a terminal deoxynucleotidyl transferase (TdT) variant comprising an amino acid sequence at least sixty percent 60% identical to an amino acid sequence selected from SEQ ID NO: 3, 4, 5, 6, 7, 8, 9, 10, 11, 12, 13, 14, 15 or 16 and comprising a substitution of histidine at position 337 with respect to SEQ ID NOs 3, 8, 10 and 14, or histidine at position 336 with respect to SEQ ID NOs 4 and 5, or histidine at position 343 with respect to SEQ ID NOs 7 and 9, or histidine at position 340 with respect to SEQ ID NOs 13 and 16, or histidine at position 332 with respect to SEQ ID NO 6, or histidine at position 338 with respect to SEQ ID NO 11, or histidine at position 335 with respect to SEQ ID NO 12, or histidine at position 350 with respect to SEQ ID NO 15, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. In regard to (ii). such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'-O-(2-nitrobenzyl)-nucleoside triphosphate, or a 3'-O-propargyl-nucleoside triphosphate. In some embodiments, the amino acid substitution of histidine is selected from the group consisting of Y, F, N and D. In some embodiments, the substitution of histidine may be in combination with other mutations described herein, such as those at the glutamine or lysine above, or the alanine, tryptophan, glycine or glutamine below.

In some embodiments, the invention is directed to a terminal deoxynucleotidyl transferase (TdT) variant comprising an amino acid sequence at least sixty percent 60% identical to an amino acid sequence selected from SEQ ID NO: 3, 4, 5, 6, 8, 9, 10, 11, 12, 13, 14 or 15 and comprising a substitution of tryptophan at position 377 with respect to SEQ ID NOs 3, 8, 10 and 14, or tryptophan at position 376 with respect to SEQ ID NO: 4 and 5, or tryptophan at position 372 with respect to SEQ ID NO 6, or tryptophan at position 380 with respect to SEQ ID NO 13, or tryptophan at position 383 with respect to SEQ ID NO 9, of tryptophan at position 378 with respect to SEQ ID NO 11, or tryptophan at position 375 with respect to SEQ ID NO 12, or tryptophan at position 380 with respect to SEQ ID NO 13, or tryptophan at position 390 with respect to SEQ ID NO 15, wherein the TOT variant (i) is capable of synthesizing a nucleic acid fragment without a template and (ii) is capable of incorporating a 3'-O-modified nucleotide onto a free 3'-hydroxyl of a nucleic acid fragment, In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate. In some embodiments, tryptophan is substituted with R or K. In some embodiments, tryptophan is substituted with R. In some embodiments, the substitution of tryptophan may be in combination with other mutations described herein, such as those at the glutamine, lysine or histidine above, or the alanine, or glycine, or glutamine below.

In some embodiments, the invention is directed to a terminal deoxynucleotidyl transferase (TdT) variant comprising an amino acid sequence at least sixty percent 60% identical to an amino acid sequence selected from SEQ ID NO: 3, 4, 5, 6, 8, 10, 11, 13, 14, 15 or 16 with a substitution of alanine at position 17 with respect to SEQ ID NOs 3, 4, 5, 6, 8, 10, 13, 14 and 15, or alanine at position 18 with respect to SEQ ID NO: 11 and 16, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. In regard to (iii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate. In some embodiments, the above substitution for alanine is V, I or L. In some embodiments, the above substitution for alanine is V. In some embodiments, the substitution of alanine may be in combination with other mutations described herein, such as those at the glutamine, lysine, histidine or tryptophan above, or the glycine or glutamine below.

In some embodiments, the invention is directed to a terminal deoxynucleotidyl transferase (TdT) variant comprising an amino acid sequence at least sixty percent 60% identical to an amino acid sequence selected from SEQ ID NO: 3, 9, 11 or 15 with a substitution of glycine at position 57 with respect to SEQ ID NOs 3 and 15, or glycine at position 58 with respect to SEQ ID NO: 9 and 11, wherein the TdT variant (i) is capable of synthesizing a nucleic acid fragment without a template and (ii) is capable of incorporating a 3-O-modified nucleotide onto a free 3 -hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs: in some embodiments, the above percent identity value is at least 97 percent identity; in some embodiments, the above percent identity value is at least 98 percent identity; in some embodiments, the above percent identity value is at least 99 percent identity. In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate. In some embodiments, the above substitution for glycine is E. In some embodiments, the substitution of glycine may be in combination with other mutations described herein, such as those at the glutamine, lysine, histidine, tryptophan or alanine above and/or the glutamine described below.

In some embodiments, the invention is directed to a terminal deoxynucleotidyl transferase (TdT) variant comprising an amino acid sequence at least sixty percent 60% identical to an amino acid sequence selected from SEQ ID NO: 3, 4, or 6and comprising a substitution of glutamine at position 261 with respect to SEQ ID NO: 3, or glutamine at position 262 with respect to SEQ ID NO: 6, or glutamine at position 264 with respect to SEQ ID NO 4, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity: in some embodiments, the above percent identity value is at least 98 percent identity; in some embodiments, the above percent identity value is at least 99 percent identity. In regard to (ii), such 3'-O-modified nucleotide may comprise a 3'-O—NH2-nucleoside triphosphate, a 3ª-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate. In some embodiments, the amino acid substitution of glutamine is R. In some embodiments, the substitution of glutamine at this position may be in combination with other mutations described herein, such as those at the glutamine, histidine, lysine, alanine. tryptophan or glycine above.

In some embodiments, the invention is directed to a terminal deoxynucleotidyl transferase (TdT) variant comprising an amino acid sequence at least ninety percent identical to the amino acid sequence as set forth in SEQ ID NO: 4 with substitutions at position M63. R207, R324 and E327. In some embodiments, the invention is directed to a terminal deoxynucleotidyl transferase (TdT) variant comprising or consisting in an amino acid sequence at least ninety percent identical to the amino acid sequence as set forth in SEQ ID NO: 24 with substitutions at positions M47, R190, R308 and E311. In some embodiments, the invention is directed to a terminal deoxynucleotidyl transferase (TdT) variant comprising or consisting in an amino acid sequence at least ninety percent identical to the amino acid sequence as set forth in SEQ ID NO: 26 with substitutions at positions M46, R190 and E311. In a particular embodiment, at least one of the amino acid substitutions is selected from the group consisting in M46R, M47R, M63R, R190L, R207L, E227N and E311N. In some embodiments, the invention is directed to a terminal deoxynucleotidyl transferase (TdT) variant comprising an amino acid sequence at least ninety percent identical to the amino acid sequence as set forth in SEQ ID NO: 25 with substitutions at positions R184, R306 and E309. Particularly, the substitutions are selected from the group consisting in R184L, R306A and E309N. In an embodiment, the variant consists in an amino acid sequence having at least 90% identity with the amino acid sequence set forth in SEQ ID NO: 25 with the substitutions R184L, R306A and E309N.

In some embodiments, a TdT variant of the invention comprises substitutions of glutamine (first occurrence above), lysine, histidine, tryptophan, alanine, glycine and glutamine (second occurrence above) at the indicated positions and specified SEQ ID NOs described above.

In some embodiments, a TdT variant of the invention comprises an isolated protein.

In addition to the above TdT variants which comprise one or more substitutions of glutamine, lysine, histidine, tryptophan, alanine and/or glycine at the indicated positions of the specified SEQ ID NOs, in some embodiments, each such TdT variant may further comprise from 1 to 11 additional substitutions selected from the positions listed in the rows of Table 1 (set forth in FIG. 2) for the specified SEQ ID NO. Such additional substitutions are sometimes referred to herein as "supplemental substitutions" and contribute to an increased efficiency or rate of incorporation of 3'-O-modified nucleoside triphosphates onto a polynucleotide. In some embodiments, the supplemental substitutions are selected from Table 1. For example, a TdT variant with arginine substituted for glutamine at position 326 of SEQ ID NO 3 (as described above) may further comprise the following substitutions: L52F, M63R, A 108V and L131P (that is, substitutions for the first four positions listed in row 2 of Table 1). Thus, in this example, the TdT variant may be characterized as follows using the nomenclature described below: Q326R+L52F+M63R+A108V+L131P with respect to SEQ ID NO: 3, and otherwise comprising at least 90 percent sequence identity with SEQ ID NO 3.

In another example, a TdT variant with arginine substituted for glutamine at position 325 of SEQ ID NO 5, aspartic acid substituted for histidine at position 336 of SEQ ID NO 5, and arginine substituted for tryptophan at position 376 of SEQ ID NO 5, may further comprise the substitutions M63R, A110V, L131P, C173G, R207N, E294A, R325P, E327N and R353K. (selected from row 4 of Table 1, set forth in FIG. 2). Thus, in this example, the TdT variant may be characterized as Q325R+H336D+W376D+M63R+A110V+ L131P +C173G+R207N+E294A+R325P+E327N+R353K with respect to SEQ ID NO: 5, and otherwise comprise a specified percent sequence identity, such as at least 90 percent sequence identity, with SEQ ID NO: 5.

In addition to the above TdT variants which comprise one or more substitutions of glutamine, lysine, histidine, tryptophan, alanine and/or glycine at the indicated positions of the specified SEQ ID NOs, and in addition to the Supplemental Substitutions described above, in some embodiments, each such TdT variant may further comprise from 1 to 12 additional substitutions selected from the positions listed in the rows of Table 2 (set forth in FIG. 3) for the specified SEQ ID NO. Such additional substitutions are sometimes referred to herein as "Stability Substitutions" and contribute to an increased stability of a TdT variant, particularly with respect to reaction conditions of template-free enzymatic polynucleotide incorporation, and with respect to elevated temperature. For example, a TdT variant may comprise substitutions A17V, K265E and W377R from Table 3B, supplemental substitutions M63R. L131P, C173G, R207L, G284L and R325P from Table 1, and stability substitutions S119A and S146E from Table 2, wherein the position numbers are with respect to SEQ ID NO: 3. Such TdT variant may be designated as A17V+M63R+S119A+ L131P+S146E+C173G+R207L+K265E+G284L+R325P+ W377R and it is understood that in addition to these specific substitution the TdT variant comprises a specified percent sequence identity, such as at least 90 percent sequence identity, with SEQ ID NO: 3.

In some embodiments, a TdT variant of the invention comprises all or part of a BRCT-like segment attached to its N-terminus, e.g. see Delarue et al, EMBO J., 21(3): 427-439 (2002).

In some embodiments, the invention is directed to TdT variants comprising an amino acid sequence that has at least 90 percent identity with SEQ ID NO: 1, wherein each such TdT variant (i) comprises at least one mutation at one or more positions selected from the group consisting of G186, S248, T331, Q390, K394, Q455 or H466 with respect to SEQ ID NO: 1, or a functional equivalent thereof, and (ii) is capable of extending a polynucleotide without a template, and (iii) is capable of incorporating 3'-O-modified nucleoside triphosphates with greater efficiency than a wild type TdT. In some embodiments, TdT variants of the invention comprise G186E. In some embodiments, TdT variants of the invention comprise K394 E/T/A/R. In some embodiments, the invention is directed to TdT variants comprising an amino acid sequence that has at least 90 percent identity with SEQ ID NO: 3, wherein each such TdT variant (i) comprises at least one mutation at one or more positions selected from the group consisting of G57, S119, T202, Q261, K265, Q326 or H337 with respect to SEQ ID NO: 3, or a functional equivalent thereof, and (ii) is capable of extending a polynucleotide without a template, and (iii) is capable of incorporating 3'-O-modified nucleoside triphosphates with greater efficiency than a wild type TdT.

In the embodiments of this paragraph, the amino acid position numbers are with respect to SEQ ID NO: 3. In some embodiments, TdT variants of the invention comprise G57E. In some embodiments, TdT variants of the invention comprise K265E/T/A/R. In some embodiments, TdT variants of the invention comprise T202A. In some embodiments, TdT variants of the invention comprise Q326T/F/L/M or Q326T/ F/L/M/I/V/Y. In some embodiments, TdT variants of the invention comprise S119A. In some embodiments, TdT variants of the invention comprise Q261R. In some embodiments, TdT variants of the invention comprise H337Y/F/D. In some embodiments, TdT variants of the invention comprise one or more amino acid changes selected from the group consisting of T202A, Q326T/F/U/M or Q326T/F/L/ M/I/V/Y/W, S119A, Q261R, H337Y/F/D, G57B and K265E/T/A/R. In some embodiments, TdT variants of the invention comprise K265E/T/A; and in other embodiments comprise both G57E and K265E/T/A. In some embodiments, variant TdTs of the invention have at least 95 percent identity with the reference or wild type TdT sequence SEQ ID NO: 3. In some embodiments, variant TdTs of the invention have at least 98 percent identity with SEQ ID NO: 3. In some embodiments, TdT variants of the invention displaying increase efficiency of incorporation comprise one or more amino acid changes selected from the group consisting of T202A, Q326T/F/L/M or Q326T/F/L/M/I/V/Y, Q261R, H337Y/F/D, G57E and K265E/T/A/R. In some embodiments, TdT variants of the invention displaying enhanced stability comprise the amino acid change S119A. In some embodiments, TdT variants of the invention displaying increased efficiency of incorporation comprise, either individually or in combination, G57E, K265T/E/R/A, Q326T/F/L/M, or H337Y/F/D.

The invention further relates to the use of a TdT variant of the invention for synthesizing a nucleic acid molecule without template by the successive addition of one or more 3'-O-modified nucleotides to a nucleic acid fragment. In some embodiments, such methods comprise the steps of (a) providing an initiator comprising an oligonucleotide having a free 3'-hydroxyl; (b) reacting under enzymatic extension conditions a TdT variant of the invention with the initiator or an extended initiator in the presence of a 3'-O-reversibly blocked nucleoside triphosphate. In some embodiments, such method further includes steps of (c) deblocking the extended initiators to form extended initiators with free 3'-hydroxyls and (d) repeating steps (b) and (c) until a nucleic acid molecule of a predetermined sequence is synthesized.

In further embodiments, the invention includes nucleic acid molecules encoding a variant TdTs described above, expression vectors comprising such nucleic acid molecules, and host cells comprising the aforementioned nucleic acid molecules or the aforementioned expression vectors. In still further embodiments, the invention includes processes for producing a variant TdT of the invention, wherein a host cell is cultivated under culture conditions allowing the expression of the nucleic acid encoding said variant TdT, and wherein the variant TdT is optionally retrieved. The invention also includes kits for performing template-free polynucleotide elongations of any predetermine sequence, wherein the kits include a TdT variant of the invention. Such kits may further comprise 3'-O-blocked deoxyribonucleoside triphosphates (dNTPs) for A, C, G and T for DNA elongation, or 3'-O-blocked ribonucleoside triphosphates (rNTPs) for rA, rC, rG and U for RNA elongation.

The present invention advantageously overcomes problems in the field of template-free enzymatic nucleic acid synthesis related to the efficient incorporation of 3'-O-modified nucleoside triphosphates by providing new TdT variants with a capability of incorporating 3'-O-modified nucleotides with greater efficiency or at a higher rate than wild type TdTs or previously available TdT variants, particularly with respect to incorporation of nucleotides onto polynucleotides that comprise certain 3' nucleotide sequences described herein. In some embodiments, the present invention also advantageously overcomes problems in the above field by providing new TdT variants with increased stability in comparison with wild type TdTs.

BRIEF DESCRIPTION OF THE DRAWINGS

FIG. 2 contains Table 1 listing supplementary substitutions for the various SEQ ID NOs.

FIG. 3 contains Table 2 listing stability substitutions for the various SEQ ID NOs.

DETAILED DESCRIPTION OF THE INVENTION

Figure 1:
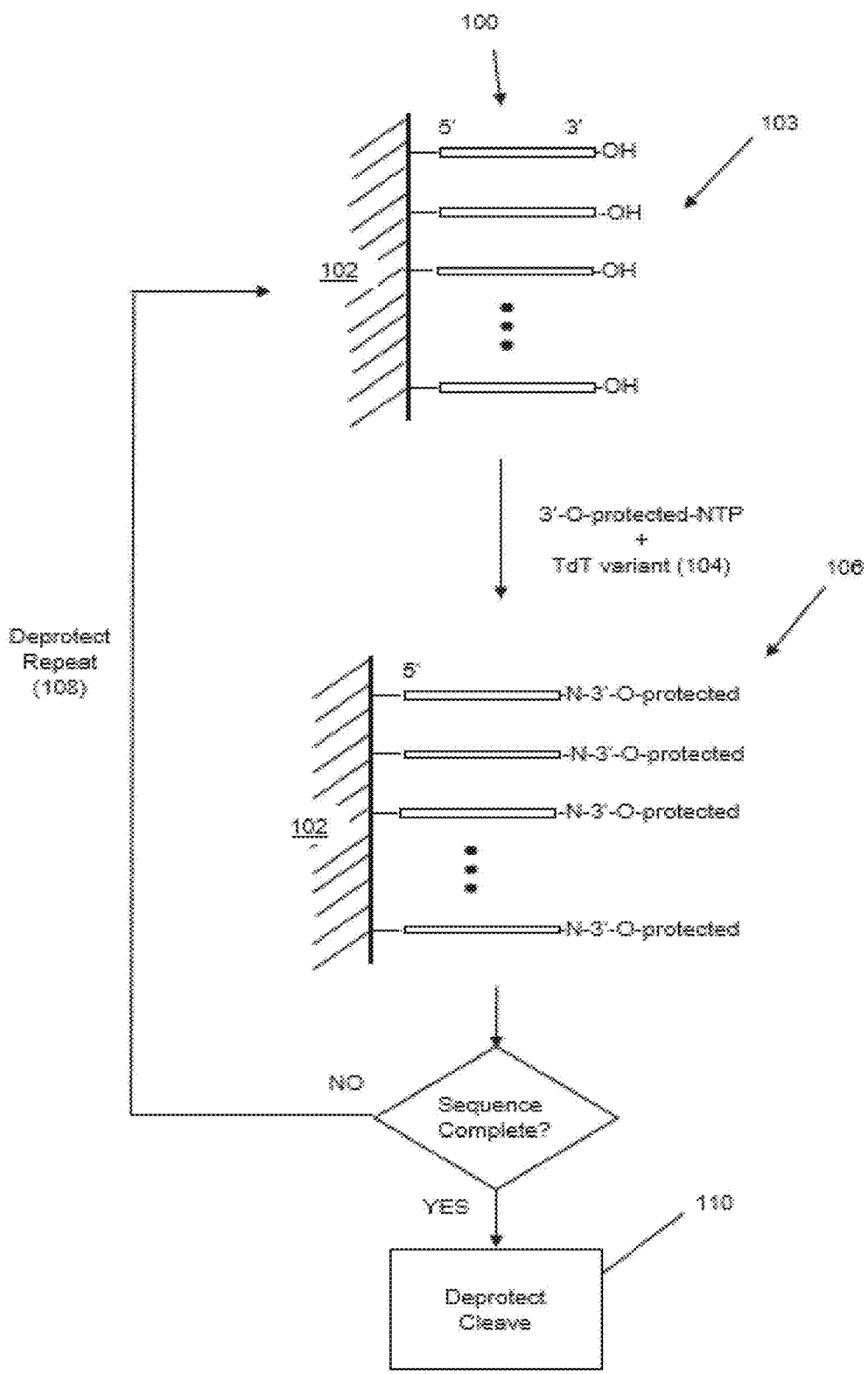
FIG. 1 illustrates diagrammatically the steps of a method of template-free enzymatic nucleic acid synthesis using TdT variants of the invention.

While the invention is amenable to various modifications and alternative forms, specifies thereof have been shown by way of example in the drawings and will be described in detail. It should be understood that the intention is not to limit the invention to the particular embodiments described. It is the intention to cover all modifications, equivalents, and alternatives falling within the spirit and scope of the invention. Guidance for aspects of the invention is found in many available references and treatises well known to those with ordinary skill in the art, including, for example, Sambrook et al. (1989), Molecular cloning: A Laboratory Manual, Cold Spring Harbor Laboratory, and the like.

The present invention provides variants of the TdT polymerase that can be used for synthesizing polynucleotides, such as DNA or RNA, of predetermined sequences without the use of template strand. The TdT variants of the invention allow modified nucleotides, and more particularly 3'O-reversibly blocked nucleoside triphosphates, to be used in an enzyme-based method of polynucleotide synthesis. The variants of the present invention are described according to their mutations or substitutions at specific residues, whose positions are designated with respect to a specified SEQ ID NO.

In some embodiments, a TdT variant may be operably linked to a linker moiety including a covalent or non-covalent bond; amino acid tag (e.g., poly-amino acid tag, poly-His tag, 6His-tag); chemical compound (e.g., polyethylene glycol); protein-protein binding pair (e.g., biotin-avidin); affinity coupling; capture probes; or any combination of these. The linker moiety can be separate from or part of a TdT variant (e.g., recombinant His-tagged polymerase, such as exemplified by the following pairs of SEQ ID NOs: 19 and 20, 21 and 22, 23 and 24, and 25 and 26). Typically, the linker moiety does not interfere with the nucleotide binding activity, or catalytic activity of the mutant TdT.

In some of the embodiments described above, the efficiency of a variant TdT in incorporating a 3'O-modified nucleoside triphosphate is at least 105 percent that of a previous available TdT wildtype or variant; in other embodiments, the efficiency of a variant TdT in incorporating a 3'O-modified nucleoside triphosphate is at least 110 percent that of a previous available TdT wildtype or variant; in other embodiments, the efficiency of a variant TdT in incorporating a 3'O-modified nucleoside triphosphate is at least 150 percent that of a previous available TdT wildtype or variant.

In some embodiments, a TdT variant of the invention comprises an amino acid sequences at least 60 percent identical to the SEQ ID NOs specified in Table 3A and comprises at least a substitution of glutamine at the position indicated in column 1 for the specified SEQ ID NO. In some embodiments, a TdT variant of the invention comprises an amino acid sequences at least 60 percent identical to the SEQ ID NOs specified in Table 3A and comprises from 1 to 7 substitutions of glutamine, lysine, histidine, tryptophan, alanine or glycine at the positions indicated in columns 1 to 7, respectively, for the specified SEQ ID NOs. In some embodiments, a TdT variant of the invention comprises an amino acid sequences at least 60 percent identical to the SEQ ID NON specified in Table 3B and comprises at least a substitution of glutamine with one of T, F, L or M at the indicated position for the specified SEQ ID NO. In some embodiments, a TdT variant of the invention comprises an amino acid sequences at least 60 percent identical to the SEQ ID NOs specified in Table 3B and comprises from 1 to 7 substitutions of glutamine with one of T, F, L or M, lysine with one of E, T, A or R, histidine with one of Y, F or D, tryptophan with R, alanine with V or glycine with E at the positions indicated in columns 1 to 7, respectively, for the specified SEQ ID NOs. Where a cell of the Table is blank at a column and specified SEQ ID NO, the amino acid associated with the column is not present in the specified SEQ ID NO so that there is no substitution at that position of the TdT variant.

Each of the TdT variants described in the previous paragraph further (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs. In some embodiments, the percent identity value of the previous paragraph is at least 90 percent identity; in some embodiments, such percent identity value is at least 95 percent identity; in some embodiments, such percent identity value is at least 98 percent identity; in some embodiments, such percent identity value is at least 99 percent identity. In some embodiments, the above-mentioned 3'-O-modified nucleotide may comprise a 3'-O—NH2-nucleoside triphosphate, a 3'-O-azidomethyl-nucleoside, triphosphate, a 3'-O-allyl-nucleoside triphosphate a 3'-(2-nitrobenzyl)-nucleoside triphosphate, or a 3 -O-propargyl-nucleoside triphosphate.

TABLE 3A

TdT variants with substitutions at positions Q455, K394, H466, W506, A146, G186 and/or Q390 (with respect to SEQ ID NO: 1) or functionally equivalent positions of the specified SEQ ID NO

| 1 | 2 | 3 | 4 | 5 | 6 | 7 | SEQ ID NO |
|---|---|---|---|---|---|---|---|
| Q455 | K394 | H466 | W506 | A146 | G186 | Q390 | 1 |
| Q326 | K265 | H337 | W377 | A17 | G57 | Q261 | 3 |
| Q325 | — | H336 | W376 | A17 | — | Q264 | 4 |
| Q325 | K264 | H336 | W376 | A17 | — | — | 5 |
| Q321 | K263 | H332 | W372 | A17 | — | Q262 | 6 |
| Q332 | K265 | H343 | — | — | — | — | 7 |
| Q326 | K265 | H337 | W377 | A17 | — | — | 8 |
| Q332 | K265 | H343 | W383 | — | G58 | — | 9 |
| Q326 | K265 | H337 | W377 | A17 | — | — | 10 |
| Q327 | K266 | H338 | W378 | A18 | G58 | — | 11 |
| Q324 | K263 | H335 | W375 | — | — | Q259 | 12 |
| Q329 | K265 | H340 | W380 | A17 | — | — | 13 |
| Q326 | K265 | H337 | W377 | A17 | — | — | 14 |
| Q339 | K272 | H350 | W390 | A17 | G57 | — | 15 |
| Q329 | K268 | H340 | — | A18 | — | — | 16 |

TABLE 3B

TdT variants with indicated substitutions at positions Q455, K394,
H466, W506, A146, G186 and/or Q390 (with respect to SEQ ID NO: 1)
or functionally equivalent positions of the specified SEQ ID NO

| 1 | 2 | 3 | 4 | 5 | 6 | 7 | SEQ ID NO |
|---|---|---|---|---|---|---|---|
| Q455T/F/L/M | K394E/T/A/R | H466Y/F/D | W506R/K | A146V/I/L | G186E | Q390R | 1 |
| Q326T/F/L/M | K265E/T/A/R | H337Y/F/D | W377R/K | A17V/I/L | G57E | Q261R | 3 |
| Q325T/F/L/M | — | H336Y/F/D | W376R/K | A17V/I/L | — | Q264R | 4 |
| Q325T/F/L/M | K264E/T/A/R | H336Y/F/D | W376R/K | A17V/I/L | — | — | 5 |
| Q321T/F/L/M | K263E/T/A/R | H332Y/F/D | W372R/K | A17V/I/L | — | Q262R | 6 |
| Q332T/F/L/M | K265E/T/A/R | H343Y/F/D | — | — | — | — | 7 |
| Q326T/F/L/M | K265E/T/A/R | H337Y/F/D | W377R/K | A17V/I/L | — | — | 8 |
| Q332T/F/L/M | K265E/T/A/R | H343Y/F/D | W383R/K | — | G58E | — | 9 |
| Q326T/F/L/M | K265E/T/A/R | H337Y/F/D | W377R/K | A17V/I/L | — | — | 10 |
| Q327T/F/L/M | K266E/T/A/R | H338Y/F/D | W378R/K | A18V/I/L | G58E | — | 11 |
| Q324T/F/L/M | K263E/T/A/R | H335Y/F/D | W375R/K | — | — | Q259R | 12 |
| Q329T/F/L/M | K265E/T/A/R | H340Y/F/D | W380R/K | A17V/I/L | — | — | 13 |
| Q326T/F/L/M | K265E/T/A/R | H337Y/F/D | W377R/K | A17V/I/L | — | — | 14 |
| Q339T/F/L/M | K272E/T/A/R | H350Y/F/D | W390R/K | A17V/I/L | G57E | — | 15 |
| Q329T/F/L/M | K268E/T/A/R | H340Y/F/D | — | A18V/I/L | — | — | 16 |

As noted above, in some embodiments, TdT variants of the invention may comprise, in addition to the substitutions set forth in Tables 3A and 3B, one or more Supplementary Substitutions at the positions listed in Table 1 (set forth in FIG. 2) with respect to the specified SEQ ID NOs, and/or one or more stability enhancing substitutions at the positions listed in Table 2 with respect to the specified SEQ ID NOs (set forth in FIG. 3).

In regard to the stability enhancing mutations of Table 2, several adjacent substitutions are believed to exert a stabilizing effect by forming salt bridges between side chains. Thus, the equivalent stabilizing effect of substitutions Q166E and D170R may be obtained by switching the positions of E and R. Accordingly, in addition to the substitutions shown in Table 2, stabilizing substitutions also include the pairs, Q166R with D170E, C188D with L189R, and S275R with Q278E.

Particular TdT variants of the invention, DS1001 to DS1018, are set forth in Table 4. Each of the TdT variants DS1001 through DS1018 comprises an amino acid sequence at least 60 percent identical to SEQ ID NO 3 and comprises the substitutions at the indicated positions. In some embodiments, TdT variants DS1001 through DS1018 comprises an amino acid sequence at least 80 percent identical to SEQ ID NO 3 and comprises the substitutions at the indicated positions; in some embodiments, TdT variants DS1001 through DS1018 comprises an amino acid sequence at least 90 percent identical to SEQ ID NO 3 and comprises the substitutions at the indicated positions; in some embodiments, TdT variants DS1001 through DS1018 comprises an amino acid sequence at least 95 percent identical to SEQ ID NO 3 and comprises the substitutions at the indicated positions; in some embodiments, TdT variants DS1001 through DS1018 comprises an amino acid sequence at least 97 percent identical to SEQ ID NO 3 and comprises the substitutions at the indicated positions; in some embodiments, TdT variants DS1001 through DS1018 comprises an amino acid sequence at least 98 percent identical to SEQ ID NO 3 and comprises the substitutions at the indicated positions; in some embodiments, TdT variants DS1001 through DS1018 comprises an amino acid sequence at least 99 percent identical to SEQ ID NO 3 and comprises the substitutions at the indicated positions.

TABLE 4

Specific TdT Variants of the Invention

| | |
|---|---|
| DS1001 (TH M27) SEQ ID NO: 17 | A17V + L52F + M63R + A108V + C173G + R207L + K265T + G284P + E289V + R325P + E328N + R351K |
| DS1002 (M44) | A17V + Q37E + D41R + L52F + G57E + M63R + S94R + G98E + A108V + S119A + L131R + S146E + Q149R + C173G + R207L + K265T + G284P + E289V + R325P + Q326F + E328N + H337D + R351K + W377R |
| DS1003 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |
| DS1004 (M45) | A17V + Q37E + D41R + L52F + G57E + M63R + S94R + G98E + A108V + S146E + Q149R + C173G + F193Y + V199M + M201V + R207L + K265T + G284P + E289V + R325A + Q326F + E328N + R351K |
| DS1005 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |
| DS1006 (M46) | L52F + A108V + R351K + A17V + Q37E + D41R + G57E+ C59R + L60D + M63R + S94R + G98E + S119A + L131R + S146E + Q149R + C173G + R207L + K265T + G284P + E289V + R325A + Q326F + E328N |
| DS1007 (M47) | L52F + A108V + R351K + A17V + Q37E + D41R + G57E + C59R + L60D + M63R + S94R + G98E + K118Q + S119A + L131R + S146E + Q149R + C173G + R207L + K265T + G284P + E289V + R325A + Q326F + E328N + W377R |

TABLE 4-continued

Specific TdT Variants of the Invention

| | |
|---|---|
| DS1008 | A17V + Q37E + D41R + L52F + G57E + C59R + L60D + M63R + S94R + G98E + A108V + S119A + L131R + S146E + Q149R + C173G + R207L + F259S + Q261L + G284P + E289V + R325A + Q326F + E328N + R351K + W377R |
| DS1009 (MS 13-34) SEQ ID NO: 18 | A17V + D41R + L53F + G57E + C59R + L60D + M63R + S94R + G98E + K118Q + S119A + L131R + S146E + Q149R + C173G + R207L + K265T + G284P + E289V + R325A + Q326F + R351K + W377R |
| DS1010 (MS 34-1) SEQ ID NO: 19 | A17V + D41R + L52F + G57E + C59R + L60D + M63R + S94R + G98E + A108V + S119A + L131R + S146E + Q149R + R207L + K265T + G284P + E289V + R325A + Q326F + R351K |
| DS1011 | A17V + D41R + L53F + G57E + C59R + L60D + M63R + S94R + G98E + K118Q + S119A + L131R + S146E + Q149R + C173G + R207L + K265T + G284P + E289V + Q326F + R351K + W377R |
| DS1012 (M48) | A17V + Q37E + D41R + L52F + G57E + C59R + L60D + M63R + S94R + G98E + A108V + S119A + L131R + S146E + Q149R + C173G + R207L + F259S + Q261L, G284P + E289V + R325A + Q326F + E328N + R351K + W377R |
| DS1013 | A17V + Q37E + D41R + L52F + G57E + M63R + S94R + G98E + A108V + S146E + Q149R + C173G + R207L + K265T + G284P + E289V + R325A + Q326F + E328N + R351K |
| DS1014 (M49) | A17V + Q37E + D41R + L52F + G57E + C59R + L60D + M63R + S94R + G98E + A108V + S119A + L131R + S146E + Q149R + C173G + R207L + E257D + F259S + K260R + Q261L + G284P + E289V + R325A + Q326F + E328N + R351K + W377R |
| DS1015 | A17V + Q37E + D41R + L52F + G57E + C59R + L60D + M63R + S94R + G98E + A108V + S119A + L131R + S146E + Q149R + C173G + F193Y + V199M + M201V + R207L + E257D + F259S + K260R + Q261L + G284P + E289V + R325A + Q326F + E328N + R351K + W377R |
| DS1016 (TH c2_5) SEQID NO: 20 | A17V + D41R + L52F + G57E + M63R + S94R + G98E + A108V + S146E + Q149R + C173G + M184T + R207L + K209H + G284L + E289A + R325V + E328K + R351K |
| DS1017 (M27) SEQID NO: 32 | A17V + L52F + G57E + M63R + A108V + C173G + R207L + K265T + G284P + E289V + R325P + E328N + R351K |
| DS1018 (M60) | A17V + L32T + Q37R + D41R + L52F + G57E + C59R + L60D + M63R + S67A + S94R + G98E + A108V + S119A +L131R + S146E + Q149R + V171A + S172E + C173R + V182I + S183E + R207L + K209H + M210K + T211I + E223G + A224P + E228D + Q261L + G284P + E289V + R325A + Q326F + E328N + R351K + D372E |

TdT variants of the invention as described above each comprise an amino acid sequence having a percent sequence identity with a specified SEQ ID NO, subject to the presence of indicated substitutions. In some embodiments, the number and type of sequence differences between a TdT variant of the invention described in this manner and the specified SEQ ID NO may be due to substitutions, deletion and/or insertions, and the amino acids substituted, deleted and/or inserted may comprise any amino acid. In some embodiments, such deletions, substitutions and/or insertions comprise only naturally occurring amino acids. In some embodiments, substitutions comprise only conservative, or synonymous, amino acid changes, as described in Grantham, Science, 185: 862-864 (1974). That is, a substitution of an amino acid can occur only among members of its set of synonymous amino acids. In some embodiments, sets of synonymous amino acids that may be employed are set forth in Table 5A.

TABLE 5A

Synonymous Sets of Amino Acids I

| Amino Acid | Synonymous Set |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Gly, Ala, Thr, Pro, Ser |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Cys, Ser, Thr |
| His | His, Glu, Lys, Gln, Thr, Arg |
| Gln | Gln, Glu, Lys, Asn, His, Thr, Arg |
| Asn | Asn, Gln, Asp, Ser |
| Lys | Lys, Glu, Gln, His, Arg |
| Asp | Asp, Glu, Asn |
| Glu | Glu, Asp, Lys, Asn, Gln, His, Arg |
| Met | Met, Phe, Ile, Val, Leu |
| Trp | Trp |

In some embodiments, sets of synonymous amino acids that may be employed are set forth in Table 5B.

TABLE 5B

Synonymous Sets of Amino Acids II

| Amino Acid | Synonymous Set |
|---|---|
| Ser | Ser |
| Arg | Arg, Lys, His |
| Leu | Ile, Phe, Met, Leu |
| Pro | Ala, Pro |
| Thr | Thr |
| Ala | Pro, Ala |

TABLE 5B-continued

Synonymous Sets of Amino Acids II

| Amino Acid | Synonymous Set |
| --- | --- |
| Val | Met, Ile Val |
| Gly | Gly |
| Ile | Met, Phe, Val, Leu, Ile |
| Phe | Met, Tyr, Ile, Leu, Phe |
| Tyr | Trp, Met |
| Cys | Cys, Ser |
| His | His, Gln, Arg |
| Gln | Gln, Glu, His |
| Asn | Asn, Asp |
| Lys | Lys, Arg |
| Asp | Asp, Asn |
| Glu | Glu, Gln |
| Met | Met, Phe, Ile, Val, Leu |
| Trp | Trp |

Measurement of Nucleotide Incorporation Activity

The efficiency of nucleotide incorporation by variants of the invention may be measured by an extension, or elongation, assay, e.g. as described in Boule et al (cited below); Bentolila et al (cited below); and Hiatt et al, U.S. Pat. No. 5,808,045. the latter of which is incorporated herein by reference. Briefly, in one form of such an assay, a fluorescently labeled oligonucleotide having a free 3'-hydroxyl is reacted under TdT extension conditions with a variant TdT to be tested for a predetermined duration in the presence of a reversibly blocked nucleoside triphosphate, after which the extension reaction is stopped and the amounts of extension products and unextended initiator oligonucleotide are quantified after separation by gel electrophoresis. By such assays, the incorporation efficiency of a variant TdT may be readily compared to the efficiencies of other variants or to that of wild type or reference TdTs, or other polymerases. In some embodiments, a measure of variant TdT efficiency may be a ratio (given as a percentage) of amount of extended product using the variant TdT over the amount of extended product using wild type TdT in an equivalent assay.

In some embodiments, the following particular extension assay may be used to measure incorporation efficiencies of TdTs: Primer used is the following:

(SEQ ID NO: 2)
5'-AAAAAAAAAAAAAGGGG-3'

The primer has also an ATTO fluorescent dye on the 5' extremity. Representative modified nucleotides used (noted as dNTP in Table 5) include 3'-O-amino-2',3'-dideoxynucleotides-5'-triphosphates (ONH2, Firebird Biosciences), such as 3'-O-amino-2',3'-dideoxyadenosine-5'-triphosphate. For each different variant tested, one tube is used for the reaction. The reagents are added in the tube, starting from water, and then in the order of Table 6. After 30 min at 37° C. the reaction is stopped by addition of formamide (Sigma).

TABLE 6

Extension Activity Assay Reagents

| Reagent | Concentration | Volume |
| --- | --- | --- |
| H$_2$O | — | 12 µL |
| Activity buffer | 10x | 2 µL |
| dNTP | 250 µM | 2 µL |
| Purified enzyme | 20 µM | 2 µL |
| Fluorescent primer | 500 nM | 2 µL |

The Activity buffer comprises, for example, TdT reaction buffer (available from New England Biolabs) supplemented with CoCl$_2$.

The product of the assay is analyzed by conventional polyacrylamide gel electrophoresis. For example, products of the above assay may be analyzed in a 16 percent polyacrylamide denaturing gel (Bio-Rad). Gels are made just before the analysis by pouring polyacrylamide inside glass plates and let it polymerize. The gel inside the glass plates is mounted on an adapted tank filed with THE buffer (Sigma) for the electrophoresis step. The samples to be analyzed are loaded on the top of the gel. A voltage of 500 to 2,000V is applied between the top and bottom of the gel for 3 to 6 h at room temperature. After separation, gel fluorescence is scanned using, for example, a Typhoon scanner (GE Life Sciences). The get image is analyzed using ImageJ software (imagej.nih.gov/ij/), or its equivalent, to calculate the percentage of incorporation of the modified nucleotides.

Hairpin completion assay. In one aspect, the invention includes methods of measuring the capability of a polymerase, such as a TdT variant, to incorporate a dNTP onto a 3' end of a polynucleotide (i.e. a "test polynucleotide"). One such method comprises providing a test polynucleotide with a free 3' hydroxyl under reaction conditions in which it is substantially only single stranded, but that upon extension with a polymerase, such as a TdT variant, forms a stable hairpin structure comprising a single stranded loop and a double stranded stem, thereby allowing detection of an extension of the 3' end by the presence of the double stranded polynucleotide. The double stranded structure may be detected in a variety of ways including, but not limited to, fluorescent dyes that preferentially fluoresce upon intercalation into the double stranded structure, fluorescent resonance energy transfer (FRET) between an acceptor (or donor) on the extended polynucleotide and a donor (or acceptor) on an oligonucleotide that forms a triplex with the newly formed hairpin stem, FRET acceptors and donors that are both attached to the test polynucleotide and that are brought into FRET proximity upon formation of a hairpin, or the like. In some embodiments, a stem portion of a test polynucleotide after extension by a single nucleotide is in the range of 4 to 6 basepairs in length; in other embodiments, such stem portion is 4 to 5 basepairs in length; and in still other embodiments, such stem portion is 4 basepairs in length. In some embodiments, a test polynucleotide has a length in the range of from 10 to 20 nucleotides; in other embodiments, a test polynucleotide has a length in the range of from 12 to 15 nucleotides. In some embodiments, it is advantageous or convenient to extend the test polynucleotide with a nucleotide that maximizes the difference between the melting temperatures of the stem without extension and the stem with extension; thus, in some embodiments, a test polynucleotide is extended with a dC or dG (and accordingly the test polynucleotide is selected to have an appropriate complementary nucleotide for stem formation).

Exemplary test polynucleotides for hairpin completion assays include p875 (5'-CAGTTAAAAACT) (SEQ ID NO: 21) which is completed by extending with a dGTP; p876 (5'-GAGTTAAAACT) (SEQ ID NO: 22) which is completed by extending with a dCTP; and p877 (5'-CAGCAAGGCT) (SEQ ID NO: 23) which is completed by extending with a dGTP. Exemplary reaction conditions for such test polynucleotides may comprise: 2.5-5 µM of test polynucleotide, 1:4000 dilution of GelRed® (intercalating dye from Biotium, Inc., Fremont, CA), 200 mM Cacodylate KOH pH 6.8, 1mM CoCl$_2$, 0-20% of DMSO and 3' ONH$_2$ dGTP and TdT at desired concentrations. Completion of the hairpin may be monitored by an increase in fluorescence of GelRed® dye using a conventional fluorimeter, such as a TECAN reader at a reaction temperature of 28-38° C., using an excitation filter set to 360 nm and an emission filter set to 635 nm.

In some embodiments of this aspect of the invention, TdT variants may be tested for their capacity for template-free incorporate of nucleoside triphosphates by the following steps: (a) combining a test polynucleotide having a free 3'-hydroxyl, a TdT variant and a nucleoside triphosphate under conditions wherein the test polynucleotide is single stranded but upon incorporation of the nucleoside triphosphate forms a hairpin having a double stranded stem region, and (b) detecting the amount of double stranded stem regions formed as a measure of the capacity of the TdT variant to incorporate the nucleoside triphosphate. In some embodiments, the nucleoside triphosphate is a 3'-O-blocked nucleoside triphosphate.

Measurement of Enzyme Stability

In some embodiments, enzyme stability means a capability of an enzyme (or variant thereof) to retain a particular activity after it has been subjected to destabilizing conditions for a period of time, such as, elevated temperature, lowered temperature, low pH, high pH, exposure to a chaotropic agent, or the like. In some embodiments, enzyme stability may be measured by exposing the enzyme to elevated temperatures, e.g. in the range of 50-70° C. for a period of time, e.g. in the range of 15-30 minutes, after which the activity of template-free elongation of an initiator stranded using a 3'-modified NTP is tested. In other embodiments, enzyme stability may be measured by exposing the enzyme to low pH, e.g. pH in the range of 1-4, for a period of time, e.g. in the range of 15-30 minutes. In some embodiments, TdT variants of the invention having enhanced stability with respect to elevated temperature display template-free initiator elongation activity using 3'-O-modified dNTPs equal to or greater than that of wild type TdT. In some embodiments, TdT variants of the invention having enhanced stability with respect to pH display template-free initiator elongation activity using 3'-O-modified dNTPs equal to or greater than that of wild type TdT. In some embodiments, such elevated temperature or pH stability is with respect to template-free initiator elongation activity using 3'-O-amine protected dNTPs.

Template-Free Enzymatic Synthesis

Template-free enzymatic synthesis of polynucleotides may be carried out by a variety of known protocols using template-free polymerases, such as terminal deoxynucleotidyl transferase (TdT), including variants thereof engineered to have improved characteristics, such as greater temperature stability or greater efficiency in the incorporation of 3'-O-blocked deoxynucleoside triphosphates (3'-O-blocked dNTPs), e.g. Ybert et al. International patent publication WO/2015/159023; Ybert et al, International patent publication WO/2017/216472; Hyman, U.S. Pat. No. 5,436,143; Hiatt et al, U.S. Pat. No. 5,763,594; Jensen et al, Biochemistry, 57: 1821-1832 (2018); Mathews et al, Organic & Biomolecular Chemistry, DOI: 0.1039/c6ob01371f (2016); Schmitz et al, Organic Lett., 1(11): 1729-1731 (1999).

In some embodiments, the method of enzymatic DNA synthesis comprises repeated cycles of steps, such as are illustrated in FIG. 1, in which a predetermined nucleotide is added in each cycle. Initiator polynucleotides (100) are provided, for example, attached to solid support (102), which have free 3'-hydroxyl groups (103). To the initiator polynucleotides (100) (or elongated initiator polynucleotides in subsequent cycles) are added a 3'-O-protected-dNTP and a TdT variant under conditions (104) effective for the enzymatic incorporation of the 3'-O-protected-dNTP onto the 3' end of the initiator polynucleotides (100) (or elongated initiator polynucleotides). This reaction produces elongated initiator polynucleotides whose 3'-hydroxyls are protected (106). If the elongated initiator polynucleotide contains a competed sequence, then the 3'-O-protection group is removed, or deprotected, and the desired sequence is cleaved from the original initiator polynucleotide. Such cleavage may be carried out using any of a variety of single strand cleavage techniques, for example, by inserting a cleavable nucleotide or cleavable linker at a predetermined location within the original initiator polynucleotide. Exemplary cleavable nucleotides or linkers include, but are not limited to, (i) a uracil nucleotide which is cleaved by uracil DNA glycosylase; (ii) a photocleavable group, such as a nitrobenzyl linker, as described in U.S. Pat. No. 5,739,386; or an inosine which is cleaved by endonuclease V. In some embodiments, a cleaved polynucleotide may have a free 5'-hydroxyl; in other embodiments, a cleaved polynucleotide may have a 5'-phosphorylated end. If the elongated initiator polynucleotide does not contain a completed sequence, then the 3'-O-protection groups are removed to expose free 3'-hydroxyls (103) and the elongated initiator polynucleotides are subjected to another cycle of nucleotide addition and deprotection.

In some embodiments, an ordered sequence of nucleotides is coupled to an initiator nucleic acid using a TdT in the presence of 3'-O-reversibly blocked dNTPs in each synthesis step. In some embodiments, the method of synthesizing an oligonucleotide comprises the steps of (a) providing an initiator having a free 3'-hydroxyl; (b) reacting under extension conditions the initiator or an extension intermediate having a free 3'-hydroxyl with a TAT in the presence of a 3'-O-blocked nucleoside triphosphate to produce a 3'-O-blocked extension intermediate: (c) deblocking the extension intermediate to produce an extension intermediate with a free 3'-hydroxyl; and (d) repeating steps (b) and (c) until the polynucleotide is synthesized. (Sometime "an extension intermediate" is also referred to as an "elongation fragment."). In some embodiments, an initiator is provided as an oligonucleotide attached to a solid support, e.g. by its 5' end. The above method may also include washing steps after the reaction, or extension, step, as well as after the de-blocking step. For example, the step of reacting may include a sub-step of removing unincorporated nucleoside triphosphates, e.g. by washing, after a predetermined incubation period, or reaction time. Such predetermined incubation periods or reaction times may be a few seconds, e.g. 30 sec, to several minutes, e.g. 30 min.

The above method may also include capping step(s) as well as washing steps after the reacting, or extending, step, as well as after the deblocking step. As mentioned above, in some embodiments, capping steps may be included in which non-extended free 3'-hydroxyls are reacted with compounds that prevents any further extensions of the capped strand. In some embodiments, such compound may be a dideoxynucleoside triphosphate. In other embodiments, non-extended strands with free 3'-hydroxyls may be degraded by treating them with a 3'-exonuclease activity, e.g. Exo I. For example, see Hyman, U.S. Pat. No. 5,436,143. Likewise, in some embodiments, strands that fail to be deblocked may be treated to either remove the strand or render it inert to further extensions.

In some embodiments that comprise serial synthesis of oligonucleotides, capping steps may be undesirable as capping may prevent the production of equal molar amounts of a plurality of oligonucleotides. Without capping, sequences will have a uniform distribution of deletion errors, but each of a plurality of oligonucleotides will be present in equal molar amounts. This would not be the case where non-extended fragments are capped.

In some embodiments, reaction conditions for an extension or elongation step may comprising the following: 2.0 µM purified TdT; 125-600 µM 3'-O-blocked dNTP (e.g. 3'-O—$NH_2$-blocked dNTP); about 10 to about 500 mM potassium cacodylate buffer (pH between 6.5 and 7.5) and from about 0.01 to about 10 mM of a divalent cation (e.g. $CoCl_2$ or $MnCl_2$), where the elongation reaction may be carried out in a 50 µL reaction volume, at a temperature within the range RT to 45° C., for 3 minutes. In embodiments, in which the 3'-O-blocked dNTPs are 3'-O—$NH_2$-blocked dNTPs, reaction conditions for a deblocking step may comprise the following: 700 mM $NaNO_2$; 1 M sodium acetate (adjusted with acetic acid to pH in the range of 4.8-6.5), where the deblocking reaction may be carried out in a 50 µL volume, at a temperature within the range of RT to 45° C. for 30 seconds to several minutes.

Depending on particular applications, the steps of deblocking and/or cleaving may include a variety of chemical or physical conditions, e.g. light, heat, pH, presence of specific reagents, such as enzymes, which are able to cleave a specified chemical bond. Guidance in selecting 3'-O-blocking groups and corresponding de-blocking conditions may be found in the following references, which are incorporated by reference: U.S. Pat. Nos. 5,808,045; 8,808,988; International patent publication WO91/06678; and references cited below. In some embodiments, the cleaving agent (also sometimes referred to as a de-blocking reagent or agent) is a chemical cleaving agent, such as, for example, dithiothreitol (DTT). In alternative embodiments, a cleaving agent may be an enzymatic cleaving agent, such as, for example, a phosphatase, which may cleave a 3'-phosphate blocking group. It will be understood by the person skilled in the art that the selection of deblocking agent depends on the type of 3'-nucleotide blocking group used, whether one or multiple blocking groups are being used, whether initiators are attached to living cells or organisms or to solid supports, and the like, that necessitate mild treatment. For example, a phosphine, such as tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino group. In particular embodiments, the cleaving reaction involves TCEP, a palladium complex or sodium nitrite.

As noted above, in some embodiments it is desirable to employ two or more blocking groups that may be removed using orthogonal de-blocking conditions. The following exemplary pairs of blocking groups may be used in parallel synthesis embodiments, such as those described above. It is understood that other blocking group pairs, or groups containing more than two, may be available for use in these embodiments of the invention.

| | |
|---|---|
| 3'-O—NH2 | 3'-O-azidomethyl |
| 3'-O—NH2 | 3'-O-allyl |
| 3'-O—NH2 | 3'-O-phosphate |
| 3'-O-azidomethyl | 3'-O-allyl |
| 3'-O-azidomethyl | 3'-O-phosphate |
| 3'-O-allyl | 3'-O-phosphate |

Synthesizing oligonucleotides on living cells requires mild deblocking, or deprotection, conditions, that is, conditions that do not disrupt cellular membranes, denature proteins, interfere with key cellular functions, or the like. In some embodiments, deprotection conditions are within a range of physiological conditions compatible with cell survival. In such embodiments, enzymatic deprotection is desirable because it may be carried out under physiological conditions. In some embodiments specific enzymatically removable blocking groups are associated with specific enzymes for their removal. For example, ester- of acyl-based blocking groups may be removed with an esterase, such as acetylesterase, or like enzyme, and a phosphate blocking group may be removed with a 3' phosphatase, such as T4 polynucleotide kinase. By way of example, 3'-O-phosphates may be removed by treatment with as solution of 100 mM Tris-HCl (pH 6.5) 10 mM $MgCl_2$, 5 mM 2-mercaptoethanol, and one Unit T4 polynucleotide kinase. The reaction proceeds for one minute at a temperature of 37° C.

A "3'-phosphate-blocked" or "3'-phosphate-protected" nucleotide refers to nucleotides in which the hydroxyl group at the 3'-position is blocked by the presence of a phosphate containing moiety. Examples of 3-phosphate-blocked nucleotides in accordance with the invention are nucleotidyl-3'-phosphate monoester/nucleotidyl-2',3'-cyclic phosphate, nucleotidyl-2'-phosphate monoester and nucleotidyl-2' or 3'-alkylphosphate diester, and nucleotidyl-2' or 3'-pyrophosphate. Thiophosphate or other analogs of such compounds can also be used, provided that the substitution does not prevent dephosphorylation resulting in a free 3'-OH by a phosphatase.

Further examples of synthesis and enzymatic deprotection of 3'-O-ester-protected dNTPs or 3'-O-phosphate-protected dNTPs are described in the following references: Canard et al, Proc. Natl. Acad. Sci., 92:10859-10863 (1995); Canard et al, Gene, 148: 1-6 (1994); Cameron et al. Biochemistry, 16(23): 5120-5126 (1977); Rasolonjatovo et al, Nucleosides & Nucleotides, 18(4&5): 1021-1022 (1999): Ferrero et al, Monatshefte fur Chemie, 131: 585-616 (2000); Taunton-Rigby et al, J. Org. Chem., 38(5): 977-985 (1973); Uemura et al, Tetrahedron Lett., 30(29): 3819-3820 (1989); Becker et al, J. Biol. Chem., 242(5): 936-950 (1967); Tsien, International patent publication WO1991/006678.

As used herein, an "initiator" (or equivalent terms, such as, "initiating fragment," "initiator nucleic acid," "initiator oligonucleotide," or the like) refers to a short oligonucleotide sequence with a free 3'-end, which can be further elongated by a template-free polymerase, such as TdT. In one embodiment, the initiating fragment is a DNA initiating fragment. In an alternative embodiment, the initiating fragment is an RNA initiating fragment. In one embodiment, the initiating fragment possesses between 3 and 100 nucleotides, in particular between 3 and 20 nucleotides. In one embodiment, the initiating fragment is single-stranded. In an alternative embodiment, the initiating fragment is double-stranded. In a particular embodiment, an initiator oligonucleotide synthesized with a 5'-primary amine may be covalently linked to magnetic beads using the manufacturer's protocol. Likewise, an initiator oligonucleotide synthesized with a 3'-primary amine may be covalently linked to magnetic beads using the manufacturer's protocol. A variety of other attachment chemistries amenable for use with embodiments of the invention are well-known in the art, e.g. Integrated DNA. Technologies brochure, "Strategies for Attaching Oligonucleotides to Solid Supports," v.6 (2014): Hermanson, Bioconjugate Techniques, Second Edition (Academic Press, 2008); and like references.

Many of the 3'-O-blocked dNTPs employed in the invention may be purchased from commercial vendors or synthesized using published techniques, e.g. U.S. Pat. No. 7,057, 026; International patent publications WO2004/005667, WO91/06678; Canard et al, Gene (cited above); Metzker et al, Nucleic Acids Research, 22: 4259-4267 (1994); Meng et al, J. Org. Chem., 14: 3248-3252 (3006); U.S. patent publication 2005/037991. In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure;

—O-Z wherein -Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')$_2$ represents a group of formula =C(R''')$_2$ wherein each R''' may be the same or different and is selected from the group comprising hydrogen and halogen atoms and alkyl groups, with the proviso that in some embodiments the alkyl of each R''' has from 1 to 3 carbon atoms; and wherein the molecule may be reacted to yield an intermediate in which each R" is exchanged for H or, where Z is —(R")$_2$—F, the F is exchanged for OH, SH or NH$_2$, preferably OH, which intermediate dissociates under aqueous conditions to afford a molecule with a free 3'-OH; with the proviso that where Z is —C(R')$_2$—S—R", both R' groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, -Z of the modified nucleotide or nucleoside is of formula —C(R')$_2$—N3. In certain embodiments, Z is an azidomethyl group.

In some embodiments, Z is a cleavable organic moiety with or without heteroatoms having a molecular weight of 200 or less. In other embodiments. Z is a cleavable organic moiety with or without heteroatoms having a molecular weight of 100 or less. In other embodiments, Z is a cleavable organic moiety with or without heteroatoms having a molecular weight of 50 or less. In some embodiments, Z is an enzymatically cleavable organic moiety with or without heteroatoms having a molecular weight of 200 or less. In other embodiments, Z is an enzymatically cleavable organic moiety with or without heteroatoms having a molecular weight of 100 or less. In other embodiments, Z is an enzymatically cleavable organic moiety with or without heteroatoms having a molecular weight of 50 or less. In other embodiments, Z is an enzymatically cleavable ester group having a molecular weight of 200 or less. In other embodiments, Z is a phosphate group removable by a 3'-phosphatase. In some embodiments, one or more of the following 3' phosphatases may be used with the manufacturer's recommended protocols: T4 polynucleotide kinase, calf intestinal alkaline phosphatase, recombinant shrimp alkaline phosphatase (e.g. available from New England Biolabs, Beverly, MA)

In a further particular embodiment, the 3'-blocked nucleotide triphosphate is blocked by either a 3'-O-azidomethyl, 3'-O—NH$_2$ or 3'-O-allyl group.

In still other embodiment, 3'-O-blocking groups of the invention include 3'-O-methyl, 3'-O-(2-nitrobenzyl), 3'-O)-allyl, 3'-O)-amine, 3'-O-azidomethyl, 3'-O-tert-butoxy ethoxy, 3'-O-(2-cyanoethyl), and 3'-O-propargyl.

Production of Variant TdTs

Variants of the invention may be produced by mutating known reference or wild type TdT-coding polynucleotides, then expressing it using conventional molecular biology techniques. For example, the mouse TdT gene (SEQ ID NO: 1) may be assembled from synthetic fragments using conventional molecular biology techniques, e.g. using protocols described by Stemmer et al, Gene, 164: 49-53 (1995); Kodumal et al, Proc. Natl. Acad. Sci., 101: 15573-15578 (2004); or the like, or it may be directly cloned from mouse cells using protocols described by Boule et al, Mol. Biotechnology, 10: 199-208 (1998), or Bentolila et al, EMBO J., 14: 4221-4229 (1995); or the like.

For example, an isolated TdT gene may be inserted into an expression vector, such as pET32 (Novagen) to give a vector pCTdT which then may be used to make and express variant TdT proteins using conventional protocols. Vectors with the correct sequence may be transformed in E. coli producer strains.

Transformed strains are cultured using conventional techniques to pellets from. which TdT protein is extracted. For example, previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1 h 30 at 10,000 rpm. Centrifugate is pass through a 0.2 μm filter to remove any debris before column purification.

TdT protein may be purified from the centrifugate in a one-step affinity procedure. For example, Ni-NTA affinity column (GE Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5, 500 mM NaCl (Sigma) and 0.5M imidazole (Sigma). Fractions corresponding to the highest concentration of polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH4]2SO4). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 µL of various fraction of the purified enzymes are analyzed in SDSPAGE gels.

Kits for Practicing Methods of the Invention

The invention includes a variety of kits for practicing methods of the invention. In one aspect, kits of the invention comprise a TdT variant of the invention in a formulation suitable for carrying out template-free enzymatic polynucleotide synthesis as described herein. Such kits may also include synthesis buffers that provide reaction conditions for optimizing the template-free addition or incorporation of a 3'-O-protected dNTP to a growing strand. In some embodiments, kits of the invention further include 3'-O-reversibly protected dNTPs. In such embodiments, the 3'-O-reversibly protected dNTP's may comprise 3'-O-amino-dNTPs or 3'-O-azidomethyl-dNTPs. In further embodiments, kits may include one or more of the following items, either separately or together with the above-mentioned items: (i) deprotection reagents for carrying out a deprotecting step as described herein, (ii) solid supports with initiators attached thereto, (iii) cleavage reagents for releasing completed polynucleotides from solid supports, (iv) wash reagents or buffers for removing unreacted 3'-O-protected dNTPs at the end of an enzymatic addition or coupling step, and (v) post-synthesis processing reagents, such as purification columns, desalting reagents, eluting reagents, and the like.

In regard to items (ii) and (iii) above, certain initiators and cleavage reagents go together. For example, an initiator comprising an inosine cleavable nucleotide may come with au endonuclease V cleavage reagent; an initiator comprising a nitrobenzyl photocleavable linker may come with a suitable light source for cleaving the photocleavable linker; an initiator comprising a uracil may come with a uracil DNA glycosylase cleavage reagent; and the like.

Example 1: Generation, Expression and Purification of TdT Variants

Expression strain generation. The TdT mouse gene may be generated from the pET28 plasmid described in [Boulé et al., 1998. Mol. Biotechnol. 10, 199-208]. For example, the gene may be amplified by using the following primers:

```
T7-pro:
                                    (SEQ ID No. 33)
TAATACGACTCACTATAGGG T7-ter:
                                    (SEQ ID No. 34)
GCTAGTTATTGCTCAGCGG
``` through standard molecular biology techniques. The sequence is then cloned into plasmid pET32 backbone to give the new pCTdT plasmid. After sequencing pCTdT is transformed into commercial E. coli cells, BL21 (DE3, from Novagen). Growing colonies on plate with kanamycin are isolated and named Ec-CTdT, Polymerase variants generation. The pCTdT vector is used as starting vector. Specific primers comprising one or several point mutations have been generated from Agilent online software (http://www.genomics.agilent.com:80/primerDesignProgram.jsp). The commercially available kit QuickChange II (Agilent) may be used to generate the desired modified polymerase comprising the targeted mutations. Experimental procedure follows the supplier's protocol, After generation of the different vectors, each of them is sequenced. Vectors with the correct sequence are transformed in E. coli producer strains. Clones able to grow on kanamycin LB-agar plates are isolated.

Expression. The Ec-CTdT and Ec-DSi or Ec-DSi' strains may be used for inoculating 250 mL erlens with 50 mL of LB media supplemented with appropriate amount of kanamycin. After overnight growth at 37° C., appropriate volumes of these pre-cultures are used to inoculate 5L erlens with 2 L. LB media with kanamycin. The initial OD for the 5 L cultures is chosen to be 0.01. The erlens are pot at 37° C. under strong agitation and the OD of the different cultures are regularly checked. After reaching an OD comprised between 0.6 and 0.9 each erlen is supplemented by the addition of 1 mL of 1 M. IPTG (Isopropyl β-D-1-thiogalactopyranoside, Sigma). The erlens are put back to agitation under a controlled temperature of 37° C. After overnight expression, the cells are harvested in several pellets. Pellets expressing the same variants are pooled and stored at −20° C., eventually for several months.

Extraction. Previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1 h 30 at 10,000 rpm. Centrifugate is pass through a 0.2 µm filter to remove any debris before column purification.

Purification. A one-step affinity procedure is used to purify the produced and extracted polymerase enzymes. A Ni-NTA affinity column (GB Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5. 500 mM NaCl (Sigma) and 0.5 M imidazole (Sigma). Fractions corresponding to the highest concentration of polymerases of interest are collected and pooled in a single sample. The pooled fractions are dialyzed against the dialysis buffer (20 mM Tris-HCL, pH 6.8, 200 mM Na Cl, 50 mM MgOAc, 100 mM [NH$_4$]$_2$SO$_4$). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 µL of various fraction of the purified enzymes are analyzed in SDS-PAGE gels.

Example 2: Efficiency of TdT Variants For Synthesizing Difficult Sequences

As noted above, the invention is based in part on a recognition and appreciation by the inventors that certain nucleotide sequences are difficult for TdTs to extend. Thus, an object of this experiment was to discover new TdT variants that exhibit enhanced capability to synthesize such difficult sequences based on comparison to an earlier TdT variant, designated M27 (SEQ ID NO: 32). In this example, a mutation library of mouse TdT (SEQ ID NO: 3) was produced based on structural information from mouse TdT, the activities of TdT variants from prior libraries, and from conventional protein engineering techniques. TdT variants from the library are expressed and purified as described above and were screened for their capability to synthesize certain difficult-to-synthesize sequences (shown in Table 7) at a higher rate than that of M27. Synthesis of the short sequences was performed by repeating 5 cycles of synthesis wherein each cycle comprises two steps: (i) an extension step (typical reaction volume 200 µL) wherein a primer (or initiator) is incubated for 3 min at 37° C. with 1 mM of a 3'-O—NH2-dXTP and a defined concentration of TdT variant in the activity buffer (X can be A, T, C or G depending on the sequence to synthesized; for example, to synthesize AACTA, X=A. for the first cycle, X=A for the second cycle, X=C for the third cycle, and so on); and (ii) a deprotection step (typical reaction volume 200 µL) to deblock the extended primer to remove the 3'-protection group and allow a second extension step. The deblocking reaction is performed in 700 mM NaNO2, 1 M Sodium Acetate, pH=5.5 for 3 min. Volume of reaction is typically 200 µL (e.g. see Benner, U.S. Pat. No. 7,544,794). The extended primer is linked to a solid support that allows removal of the reaction buffer between each step. As noted above, the reactions were run for 3 min at 37° C. after which the extended primers were (i) cleaved from their supports, (ii) separated by electrophoresis and (iii) the fluorescent intensity of the bands was measured to evaluate the efficiency of synthesis for each variant. The results are shown in Table 7 where the entries are relative values that reflect the relative extension rates among the variants.

TABLE 7

Synthesis Efficiency of Various TdT Variants

| Variant | 3' Sequences of Test Initiators | | | | |
|---|---|---|---|---|---|
|  | -AACTA | -AAGCT | -CCCCA | -GGCAT | -GGCTG |
| DS1017 (M27) SEQ ID NO: 32 | 75 | 96 | 26 | 96 | 56 |

TABLE 7-continued

Synthesis Efficiency of Various TdT Variants

| Variant | 3' Sequences of Test Initiators | | | | |
|---|---|---|---|---|---|
|  | -AACTA | -AAGCT | -CCCCA | -GGCAT | -GGCTG |
| Lib34-20 | 72 | 96 | 18 | 96 | 57 |
| DS1002 (M44-1) | 74 | 97 | 50 | 97 | 36 |
| DS1002 (M44-2) | 78 | 95 | 50 | 96 | 35 |
| DS1004 (M45) | 84 | 97 | 59 | 95 | 58 |
| DS1006 (M46) | 93 | 96 | 28 | 96 | 71 |
| DS1007 (M47) | 92 | 97 | 30 | 96 | 78 |
| Lib34-16 | 91 | 94 | 7 | 0 | 75 |

An inspection of the sequences of the variants that exceed extension activity of M27 for one or more of the test initiators showed that each one at least possessed a substitution at Q326 and usually shared one or more additional substitutions from the set K265, H337, W377, A17 and G57, with respect to SEQ ID NO: 3.

Elongation efficiency of variants M27, M44 and M45 were also measured under different reaction temperatures. In these experiments only a single elongation step was performed. The Reaction conditions were as follows: primer (i.e. initiator) concentration of 0.5 µM, a single 3'-ONH2-dTTP at 125 µM, and TdT reaction buffer (for example, available from New England Biolabs) supplemented with CoCl2. Separate reactions were run using different primers (not attached to supports) having different compositions and lengths in the range of from 20 to 25 nucleotides. Primers were labeled with an ATTO fluorescent dye on the 5' extremity. The reactions were run for 10 min separately at 37° C., 45° C., 50° C. and 55° C. The results are shown in Table 8 where the values in the Table are relative magnitudes.

TABLE 8

Optimal Extension Reaction Temperatures For Various TdT Variants

| | Incorporation on Mixed Nucleotide Primer | | | | Incorporation on PolyC Primer | | | |
|---|---|---|---|---|---|---|---|---|
| | Temperature | | | | | | | |
| | 37° C. | 45° C. | 50° C. | 55° C. | 37° C. | 45° C. | 50° C. | 55° C. |
| DS1017 (M27) SEQ ID NO: 32 | 63 | 100 | 77 | 24 | 71 | 97 | 100 | 44 |
| DS1002 (M44) | 95 | 131 | 137 | 120 | 78 | 104 | 127 | 128 |
| DS1004 (M45) | 62 | 101 | 105 | 82 | 72 | 101 | 122 | 116 |

The data show that M44 and M45 exhibit equivalently higher yields than M27 at temperatures of 50° C. and above, which is evidence of greater temperature stability.

Example 3: TdT Variants of Various Species

In this example, non-mouse TdT variants were constructed from publicly available genes and were tested to determine their ability to incorporate 3'-O-amino-dNTPs into a test polynucleotide (p877) in hairpin completion assays as described above. The TdT variants are identified in Table 9 along with their incorporation capacity as compared to mouse TdT variant, M27.

TABLE 9

Characteristics of Non-Mouse TdT Variants

| Species | Accession Number Of sources species | Percent Identity to M27 | Percent Activity Relative to M27* | SEQ ID NO |
|---|---|---|---|---|
| Bovine | NP_803461.1 | 82 | 484 | 27 |
| Related to Latmeria | XP_005999893.1 | 80 | 31 | 28 |
| Puma | XP_026918530.1 | 81 | 54 | 29 |
| N139 reptilian | XP_016851390.1 | 68 | 131 | 30 |
| Shrew | XP_006880141.1 | 82 | 57 | 31 |
| Mouse M27 | | 100 | — | 32 |

*Hairpin completion assay

Definitions

Amino acids are represented by either their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Len); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

"Functionally equivalent" in reference to a substituted residue means the substituted residue of a variant TdT has an identical functional role as a residue in a sequence of another TdT having a sequence homologous to SEQ ID NO: 1. Functionally equivalent residues may be identified by using sequence alignments, for example, using the Mutalin line alignment software (http://multalin.toulouse.inra.fr/multalin/multalin.html; 1988, Nucl. Acids Res., 16 (22), 25 10881-10890). After alignment, the functionally equivalent residues are at homologous positions on the different sequences considered. Sequence alignments and identification of functionally equivalent residues may be determined between any TdT and their natural variants, including inter-species.

"Isolated" in reference to protein means such a compound which has been identified and separated and/or recovered from a component of its natural environment or from a heterogeneous reaction mixture. Contaminant components of a natural environment or reaction mixture are materials which would interfere with a protein's function, and may include enzymes, hormones, and other proteinaceous or nonproteinaceous solutes. In some embodiments, a protein of the invention is purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. When manufactured by recombinant methodologies, an isolated protein of the invention may include the protein of the invention in situ within recombinant cells since at least one component of the protein's natural environment will not be present. Ordinarily, an isolated protein of the invention is prepared by at least one purification step.

"Kit" refers to any delivery system for delivering materials or reagents for carrying out a method of the invention. In the context of reaction assays, such delivery systems include systems and/or compounds (such as dilutants, surfactants, carriers, or the like) that allow for the storage, transport, or delivery of reaction reagents (e.g., one or more TdT variants, reaction buffers, 3'-O-protected-dNTPs, deprotection reagents, solid supports with initiators attached, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain one or more TdT variants for use in a synthesis method, while a second or additional containers may contain deprotection agents. solid supports with initiators, 3'-O-protected dNTPs, or the like.

"Mutant" or "variant," which are used interchangeably, refer to polypeptides derived from a natural or reference TdT polypeptide described herein, and comprising a modification or an alteration, i.e., a substitution, insertion, and/or deletion, at one or more positions. Variants may be obtained by various techniques well known in the art. In particular, examples of techniques for altering the DNA sequence encoding the wild-type protein, include, but are not limited to, site-directed mutagenesis, random mutagenesis, sequence shuffling and synthetic oligonucleotide construction. Mutagenesis activities consist in deleting, inserting or substituting one or several amino-acids in the sequence of a protein or in the case of the invention of a polymerase. The following terminology is used to designate a substitution: L238A denotes that amino acid residue (Leucine, L) at position 238 of a reference, or wild type, sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

"Sequence identity" refers to the number (or fraction, usually expressed as a percentage) of matches (e.g., identical amino acid residues) between two sequences, such as two polypeptide sequences or two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/ or ttp://www.ebi.ac.uk/Tools/emboss/. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

"Polynucleotide" or "oligonucleotide" are used interchangeably and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine. "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxycytidine, deoxyguanosine, deoxyadenosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al. Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

A "substitution" means that an amino acid residue is replaced by another amino acid residue. Preferably, the term "substitution" refers to the replacement of an amino acid residue by another selected from the naturally occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues. The sign "+" indicates a combination of substitutions.

The amino acids are herein represented by their one-letter or three-letters code according to the following nomenclature: A: alanine (Ala); C: cysteine (Cys); D: aspartic acid (Asp); E; glutamic acid (Glu); F: phenylalanine (Phe): G: glycine (Gly), H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

In the present document, the following terminology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

The invention claimed is:

1. A terminal deoxynucleotidyl transferase (TdT) variant comprising an amino acid sequence at least ninety percent identical to an amino acid sequence selected from SEQ ID NO: 3, 9, 11, or 15, with a G57E substitution with respect to SEQ ID NO: 3, or an amino acid sequence at least ninety percent identical to the amino acid sequence of SEQ ID NO: 27 and having an E at position 57 with respect to SEQ ID NO:3, wherein the TdT variant (i) is capable of synthesizing a nucleic acid fragment without a template and (ii) is capable of incorporating a 3'-O-modified nucleotide onto a nucleic acid fragment.

2. The TdT variant of claim 1, further comprising one or more of:
   (i) a substitution at position K265 with respect to SEQ ID NO: 3;
   (ii) a substitution at position H337 with respect to SEQ ID NO: 3;
   (iii) a substitution at position W377 with respect to SEQ ID NO: 3;
   (iv) a substitution at position A17 with respect to SEQ ID NO: 3;
   (v) a substitution at position Q326 with respect to SEQ ID NO: 3; or
   (vi) a substitution at position Q261 with respect to SEQ ID NO: 3.

3. The TdT variant of claim 2, wherein said TdT variant comprises a substitution at position K265 with respect to SEQ ID NO: 3, and wherein said substitution at position K265 is selected from the group consisting of E, T, A and R.

4. The TdT variant of claim 2, wherein said TdT comprises a substitution at position Q261 with respect to SEQ ID NO: 3, and wherein the substitution at position Q261 is R.

5. The TdT variant of claim 1, further comprising one or more of:
   (i) a substitution at position L52 with respect to SEQ ID NO: 3;
   (ii) a substitution at position M63 with respect to SEQ ID NO: 3;
   (iii) a substitution at position A108 with respect to SEQ ID NO: 3;

(iv) a substitution at position L131 with respect to SEQ ID NO: 3;
(v) a substitution at position C173 with respect to SEQ ID NO: 3;
(vi) a substitution at position R207 with respect to SEQ ID NO: 3;
(vii) a substitution at position G284 with respect to SEQ ID NO: 3;
(viii) a substitution at position E289 with respect to SEQ ID NO: 3;
(ix) a substitution at position R325 with respect to SEQ ID NO: 3;
(x) a substitution at position E328 with respect to SEQ ID NO: 3; or
(xi) a substitution at position R351 with respect to SEQ ID NO: 3.

6. The TdT variant of claim 1, further comprising one or more of:
(i) a substitution Q37E with respect to SEQ ID NO: 3;
(ii) a substitution D41R with respect to SEQ ID NO: 3;
(iii) a substitution C59R with respect to SEQ ID NO: 3;
(iv) a substitution L60D with respect to SEQ ID NO: 3;
(v) a substitution S94R with respect to SEQ ID NO: 3;
(vi) a substitution G98E with respect to SEQ ID NO: 3;
(vii) a substitution S119A with respect to SEQ ID NO: 3;
(viii) a substitution S146E with respect to SEQ ID NO: 3;
(ix) a substitution Q149R with respect to SEQ ID NO: 3;
(x) a substitution F193Y with respect to SEQ ID NO: 3;
(xi) a substitution V199M with respect to SEQ ID NO: 3.

7. A method of synthesizing a polynucleotide having a predetermined sequence, the method comprising the steps of:
(a) providing an initiator having a 3'-terminal nucleotide having a free 3'-hydroxyl;
(b) repeating cycles of (i) contacting under elongation conditions the initiator or elongated fragments having free 3'-O-hydroxyls with a 3'-O-blocked nucleoside triphosphate and a TdT variant according to claim 1, so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until the polynucleotide is formed.

8. A kit for performing a nucleotide incorporation reaction comprising:
(a) a TdT variant of claim 1; and
(b) one or more 3'-O-modified nucleotides.

* * * * *

```
                            SEQUENCE LISTING

Sequence total quantity: 34
SEQ ID NO: 1            moltype = AA  length = 510
FEATURE                 Location/Qualifiers
REGION                  1..510
                        note = TdT PROTEIN
source                  1..510
                        mol_type = protein
                        organism = synthetic construct
SEQUENCE: 1
MDPLQAVHLG PRKKRPRQLG TPVASTPYDI RFRDLVLFIL EKKMGTTRRA FLMELARRKG   60
FRVENELSDS VTHIVAENNS GSDVLEWLQL QNIKASSELE LLDISWLIEC MGAGKPVEMM  120
GRHQLVVNRN SSPSPVPGSQ NVPAPAVKKI SQYACQRRTT LNNYNQLFTD ALDILAENDE  180
LRENEGSCLA FMRASSVLKS LPFPITSMKD TEGIPCLGDK VKSIIEGIIE DGESSEAKAV  240
LNDERYKSFK LFTSVFGVGL KTAEKWFRMG FRTLSKIQSD KSLRFTQMQK AGFLYYEDLV  300
SCVNRPEAEA VSMLVKEAVV TFLPDALVTM TGGFRRGKMT GHDVDFLITS PEATEDEEQQ  360
LLHKVTDFWK QQGLLLYCDI LESTFEKFKQ PSRKVDALDH FQKCFLILKL DHGRVHSEKS  420
GQQEGKGWKA IRVDLVMCPY DRRAFALLGW TGSRQFERDL RRYATHERKM MLDNHALYDR  480
TKRVFLEAES EEEIFAHLGL DYIEPWERNA                                  510

SEQ ID NO: 2            moltype = DNA  length = 18
FEATURE                 Location/Qualifiers
misc_feature            1..18
                        note = PRIMER
source                  1..18
                        mol_type = other DNA
                        organism = synthetic construct
SEQUENCE: 2
aaaaaaaaaa aaaagggg                                                18

SEQ ID NO: 3            moltype = AA  length = 381
FEATURE                 Location/Qualifiers
REGION                  1..381
                        note = truncated mouse sequence
source                  1..381
                        mol_type = protein
                        organism = synthetic construct
SEQUENCE: 3
NSSPSPVPGS QNVPAPAVKK ISQYACQRRT TLNNYNQLFT DALDILAEND ELRENEGSCL   60
AFMRASSVLK SLPFPITSMK DTEGIPCLGD KVKSIIEGII EDGESSEAKA VLNDERYKSF  120
KLFTSVFGVG LKTAEKWFRM GFRTLSKIQS DKSLRFTQMQ KAGFLYYEDL VSCVNRPEAE  180
AVSMLVKEAV VTFLPDALVT MTGGFRRGKM TGHDVDFLIT SPEATEDEEQ QLLHKVTDFW  240
KQQGLLLYCD ILESTFEKFK QPSRKVDALD HFQKCFLILK LDHGRVHSEK SGQQEGKGWK  300
AIRVDLVMCP YDRRAFALLG WTGSRQFERD LRRYATHERK MMLDNHALYD RTKRVFLEAE  360
SEEEIFAHLG LDYIEPWERN A                                           381

SEQ ID NO: 4            moltype = AA  length = 380
FEATURE                 Location/Qualifiers
REGION                  1..380
                        note = Bovine truncated catalytic domain
source                  1..380
                        mol_type = protein
                        organism = synthetic construct
SEQUENCE: 4
DYSATPNPGF QKTPPLAVKK ISQYACQRKT TLNNYNHIFT DAFEILAENS EFKENEVSYV   60
TFMRAASVLK SLPFTIISMK DTEGIPCLGD KVKCIIEEII EDGESSEVKA VLNDERYQSF  120
KLFTSVFGVG LKTSEKWFRM GFRSLSKIMS DKTLKFTKMQ KAGFLYYEDL VSCVTRAEAE  180
AVGVLVKEAV WAFLPDAFVT MTGGFRRGKM IGHDVDFLIT SPGSAEDEEQ LLPKVINLWE  240
KKGLLLYYDL VESTFEKFKL PSRQVDTLDH FQKCFLILKL HHQRVDSSKS NQQEGKTWKA  300
IRVDLVMCPY ENRAFALLGW TGSRQFERDI RRYATHERKM MLDNHALYDK TKRVFLKAES  360
EEEIFAHLGL DYIEPWERNA                                             380

SEQ ID NO: 5            moltype = AA  length = 380
```

```
FEATURE                  Location/Qualifiers
REGION                   1..380
                         note = Human truncated
source                   1..380
                         mol_type = protein
                         organism = synthetic construct
SEQUENCE: 5
DYSDSTNPGP  PKTPPIAVQK  ISQYACQRRT  TLNNCNQIFT  DAFDILAENC  EFRENEDSCV   60
TFMRAASVLK  SLPFTIISMK  DTEGIPCLGS  KVKGIIEEII  EDGESSEVKA  VLNDERYQSF  120
KLFTSVFGVG  LKTSEKWFRM  GFRTLSKVRS  DKSLKFTRMQ  KAGFLYYEDL  VSCVTRAEAE  180
AVSVLVKEAV  WAFLPDAFVT  MTGGFRRGKK  MGHDVDFLIT  SPGSTEDEEQ  LLQKVMNLWE  240
KKGLLLYYDL  VESTFEKLRL  PSRKVDALDH  FQKCFLIFKL  PRQRVDSDQS  SWQEGKTWKA  300
IRVDLVLCPY  ERRAFALLGW  TGSRQFERDL  RRYATHERKM  ILDNHALYDK  TKRIFLKAES  360
EEEIFAHLGL  DYIEPWERNA                                                  380

SEQ ID NO: 6             moltype = AA  length = 376
FEATURE                  Location/Qualifiers
REGION                   1..376
                         note = Chicken 1 truncated
source                   1..376
                         mol_type = protein
                         organism = synthetic construct
SEQUENCE: 6
QYPTLKTPES  EVSSFTASKV  SQYSCQRKTT  LNNCNKKFTD  AFEIMAENYE  FKENEIFCLE   60
FLRAASVLKS  LPFPVTRMKD  IQGLPCMGDR  VRDVIEEIIE  EGESSRAKDV  LNDERYKSFK  120
EFTSVFGV    KTSEKWFRMG  LRTVEEVKAD  KTLKLSKMQR  AGFLYYEDLV  SCVSKAEADA  180
VSSIVKNTVC  TFLPDALVTI  TGGFRRGKKI  GHDIDFLITS  PGQREDDELL  HKGLLLYCDI  240
IESTFVKEQI  PSRHVDAMDH  FQKCFAILKL  YQPRVDNSSY  NMSKKCDMAE  VKDWKAIRVD  300
LVITPFEQYA  YALLGWTGSR  QFGRDLRRYA  THERKMMLDN  HALYDKRKRV  FLKAGSEEEI  360
FAHLGLDYVE  PWERNA                                                      376

SEQ ID NO: 7             moltype = AA  length = 387
FEATURE                  Location/Qualifiers
REGION                   1..387
                         note = Possum truncated
source                   1..387
                         mol_type = protein
                         organism = synthetic construct
SEQUENCE: 7
SANPDPTAGT  LNILPPTTKT  ISQYACQRRT  TINNHNQRFT  DAFEILAKNY  EFKENDDTCL   60
TFMRAISVLK  CLPFEVVSLK  DTEGLPWIGD  EVKGIMEEII  EDGESLEVQA  VLNDERYQSF  120
KLFTSVFGVG  LKTADKWYRM  GFRTLNKIRS  DKTLKLTKMQ  KAGLCYYEDL  IDCVSKAEAD  180
AVSLLVQDAV  WTFLPDALVT  ITGGFRRGKE  FGHDVDFLIT  SPGAEKEQED  QLLQKVTNLW  240
KKQGLLLYCD  LIESTFEDLK  LPSRKIDALD  HFQKCFLILK  LYHHKEDKRK  WEMPTGSNES  300
EAKSWKAIRV  DLVVCPYDRY  AFALLGWSGS  RQFERDLRRY  ATHEKKMMLD  NHALYDKTKK  360
IFLKAKSEEE  IFAHLGLEYI  QPSERNA                                         387

SEQ ID NO: 8             moltype = AA  length = 381
FEATURE                  Location/Qualifiers
REGION                   1..381
                         note = New truncated shrew
source                   1..381
                         mol_type = protein
                         organism = synthetic construct
SEQUENCE: 8
DCPASHDSSP  QKTESAAVQK  ISQYACQRRT  TLNNHNHIFT  DAFEILAENC  EFRENEGSYV   60
TYMRAASVLK  SLPFSIISMK  DTEGIPCLAD  KVKCVIEEII  EDGESSEVKA  VLNDERYKSF  120
KLFTSVFGVG  LKTAEKWFRL  GFRTLSGIMN  DKTLKLTHMQ  KAGFLYYEDL  VSCVTRAEAE  180
AVGVLVKEAV  WAFLPDAIVT  MTGGFRRGKK  VGHDVDFLIT  SPEATEEQEQ  QLLHKVITFW  240
EKEGLLLYCD  LYESTFEKLK  MPSRKVDALD  HFQKCFLILK  LHRECVDDGT  SSQLQGKTWK  300
AIRVDLVVCP  YECRAFALLG  WTGSPQFERD  LRRYATHERK  MMLDNHALYD  KTKRKFLSAD  360
SEEDIFAHLG  LDYIEPWERN  A                                               381

SEQ ID NO: 9             moltype = AA  length = 387
FEATURE                  Location/Qualifiers
REGION                   1..387
                         note = Python truncated
source                   1..387
                         mol_type = protein
                         organism = synthetic construct
SEQUENCE: 9
EKYQLPEDED  RSVTSDLDRD  SISEYACQRR  TTLKNYNQKF  TDAFEILAEN  YEFNENKGFC   60
TAFRRAASVL  KCLPFTIVQV  HDIEGVPWMG  KQVKGIIEDI  IEEGESSKVK  AVLDNENYRS  120
VKLFTSVFGV  GLKTSDKWYR  MGLRTLEEVK  RDKNLKLTRM  QKAGFLHYDD  LTSCVSKAEA  180
DAASLIVQDV  VWKIVPNAIV  TIAGGFRRGK  QTGHDVDFLI  TVPGSKQEEE  ELLHTVIDIW  240
KKQELLLYYD  LIESTFEDTK  LPSRKVDALD  HFQKCFAILK  VHKEREDKGN  SIRSKAFSEE  300
EIKDWKAIRV  DLVVVPFEQY  AFALLGWTGS  TQFERDLRRY  ATHEKKMMLD  NHALYDKTKK  360
IFLNAASEEE  IFAHLGLDYL  EPWERNA                                         387
```

```
SEQ ID NO: 10              moltype = AA  length = 381
FEATURE                    Location/Qualifiers
REGION                     1..381
                           note = truncated dog
source                     1..381
                           mol_type = protein
                           organism = synthetic construct
SEQUENCE: 10
DYTASPNPEL QKTLPVAVKK ISQYACQRRT TLNNYNNVFT DAFEVLAENY EFRENEVFSL    60
TFMRAASVLK SLPFTIISMK DTEGIPCLGD QVKCIIEEII EDGESSEVKA VLNDERYQSF   120
KLFTSVFGVG LKTSEKWFRM GFRTLSKIKS DKSLKFTPMQ KAGFLYYEDL VSCVTRAEAE   180
AVGVLVKEAV GAFLPDAFVT MTGGFRRGKK MGHDVDFLIT SPGSTDEDEE QLLPKVINLW   240
ERKGLLLYCD LVESTFEKLK LPSRKVDALD HFQKCFLILK LHHQRVDGGK CSQQEGKTWK   300
AIRVDLVMCP YERRAFALLG WTGSRQFERD LRRYASHERK MILDNHALYD KTKKIFLKAE   360
SEEEIFAHLG LDYIEPWERN A                                            381

SEQ ID NO: 11              moltype = AA  length = 382
FEATURE                    Location/Qualifiers
REGION                     1..382
                           note = TRUNC MOLE
source                     1..382
                           mol_type = protein
                           organism = synthetic construct
SEQUENCE: 11
GDCPASHDSS PQKTESAAVQ KISQYACQRR TTLNNHNHIF TDAFEILAEN CEFRENEGSY    60
VTYMRAASVL KSLPFSIISM KDTEGIPCLA DKVKCVIEEI IEDGESSEVK AVLNDERYKS   120
FKLFTSVFGV GLKTAEKWFR LGFRTLSGIM NDKTLKLTHM QKAGFLYYED LVSCVTRAEA   180
EAVGVLVKEA VWAFLPDAIV TMTGGFRRGK KVGHDVDFLI TSPEATEEQE QQLLHKVITF   240
WEKEGLLLYC DLYESTFEKL KMPSRKVDAL DHFQKCFLIL KLHRECVDDG TSSQLQGKTW   300
KAIRVDLVVC PYECRAFALL GWTGSPQFER DLRRYATHER KMMLDNHALY DKTKRKFLSA   360
DSEEDIFAHL GLDYIEPWER NA                                           382

SEQ ID NO: 12              moltype = AA  length = 379
FEATURE                    Location/Qualifiers
REGION                     1..379
                           note = Pika trunk
source                     1..379
                           mol_type = protein
                           organism = synthetic construct
SEQUENCE: 12
EYSANPSPGP QATPAVYKIS QYACQRRTTL NNHNHIFTDA FEILAENYEF KENEGCYVTY    60
MRAASVLKSL PFTIVSMKDT EGIPCLEDKV KSIMEEIIEE GESSEVKAVL SDERYQCFKL   120
FTSVFGVGLK TSEKWFRMGF RSLSNIRLDK SLKFTQMQKA GFRYYEDIVS CVTRAEAEAV   180
DVLVNEAVRA FLPDAFITMT GGFRRGKKIG HDVDFLITSP ELTEEDEQQL LHKVMNLWEK   240
KGLLLYHDLV ESTFEKLKQP SRKVDALDHF QKCFLIFKLY HERVGGDRCR QPEGKDWKAI   300
RVDLVMCPYE CHAFALLGWT GSRQFERDLR RYASHERKMI LDNHALYDKT KRVFLQAENE   360
EEIFAHLGLD YIEPWERNA                                               379

SEQ ID NO: 13              moltype = AA  length = 384
FEATURE                    Location/Qualifiers
REGION                     1..384
                           note = TRUNC HEDGEHOG
source                     1..384
                           mol_type = protein
                           organism = synthetic construct
SEQUENCE: 13
DASFGSNPGS QNTPPLAIKK ISQYACQRRT SLNNCNHIFT DALDILAENH EFRENEVSCV    60
AFMRAASVLK SLPFTIISMK DTKGIPCLGD KAKCVIEEII EDGESSEVKA ILNDERYQSF   120
KLFTSVFGVG LKTSEKWFRM GFRTLNKIMS DKTLKLTRMQ KAGFLYYEDL VSCVAKAEAD   180
AVSVLVQEAV WAFLPDAMVT MTGGFRRGKK LGHDVDFLIT SPGATEEEQ QLLPKVINFW   240
ERKGLLLYHD LVESTFEKLK LPSRKVDALD HFQKCFLILK LHLQHVNGVG NSKTGQQEGK   300
NWKAIRVDLV MCPYERRAFA LLGWTGSRQF ERDLRRFATH ERKMMLDNHA LYDKTKRIFL   360
KAESEEEIFA HLGLDYIDPW ERNA                                         384

SEQ ID NO: 14              moltype = AA  length = 381
FEATURE                    Location/Qualifiers
REGION                     1..381
                           note = truncated tree shrew
source                     1..381
                           mol_type = protein
                           organism = synthetic construct
SEQUENCE: 14
DHSTSPSPGP QKTPALAVQK ISQYACQRRT TLNNCNRVFT DAFETLAENY EFRENEDSSV    60
IFLRAASVLR SLPFTITSMR DTEGLPCLGD KVKCVIEEII EDGESSEVNA VLNDERYKSF   120
KLFTSVFGVG LKTSEKWFRM GFRTLSRVRS DKSLHLTRMQ QAGFLYYEDL ASCVTRAEAE   180
AVGVLVKEAV GAFLPDALVT ITGGFRRGKK TGHDVDFLIT SPGSTEEKEE ELLQKVLNLW   240
EKKGLLLYYD LVESTFEKLK TPSRKVDALD HFPKCFLILK LHHQRVDGDK PSQQEGKSWK   300
AIRVDLVMCP YERHAFALLG WTGSRQFERD LRRYATHERK MMLDNHALYD KTKRVFLKAE   360
SEEDIFAHLG LDYIEPWERN A                                            381
```

```
SEQ ID NO: 15             moltype = AA  length = 394
FEATURE                   Location/Qualifiers
REGION                    1..394
                          note = TRUNCATED PLATYPUS
source                    1..394
                          mol_type = protein
                          organism = synthetic construct
SEQUENCE: 15
LTNSAPINCM TETPSLATKQ VSQYACERRT TLNNCNQKFT DAFEILAKDF EFRENEGICL    60
AFMRAISVLK CLPFTIVRMK DIEGVPWLGD QVKSIIEEII EDGESSSVKA VLNDERYRSF   120
QLFNSVFEVG LTDNGENGIA RGFQTLNEVI TDENISLTKT TLSTSLWNYL PGFLYYEDLV   180
SCVAKEEADA VYLIVKEAVR AFLPEALVTL TGGPRRGKKI GHDVDFLISD PESGQDEQLL   240
PNIIKLWEKQ ELLLYYDLVE STFEKTKIPS RKVDAMDHFQ KCFLILKLHH QKVDSGRYKP   300
PPESKNHEAK NWKAIRVDLV MCPFEQYAYA LLGWTGSRQF ERDLRRYATH EKKMMLDNHA   360
LYDKTKKIFL KAESEEDIFT HLGLDYIEPW ERNA                              394

SEQ ID NO: 16             moltype = AA  length = 384
FEATURE                   Location/Qualifiers
REGION                    1..384
                          note = TRUNCATED JERBOA
source                    1..384
                          mol_type = protein
                          organism = synthetic construct
SEQUENCE: 16
SSELELLDVS WLIECMGAGK PVEMTGRHQL VKQTFCLPGF ILQDAFDILA ENCEFRENEA    60
SCVEFMRAAS VLKSLPFPII SVKDTEGIPW LGGKVKCVIE EIIEDGESSE VKALLNDERY   120
KSFKLFTSVF GVGLKTAERW FRMGFRTLST VKLDKSLTFT RMQKAGFLHY EDLVSCVTRA   180
EAEAVSVLVQ QAVVAFLPDA LVSMTGGFRR GKKIGHDVDF LITSPEATEE EEQQLLHKVT   240
NFPWEQKGLLL YCDHVESTFE KCKLPSRKVD ALDHFQKCFL ILKLYREVD SVKSSQQEGK   300
GWKAIRVDLV MCPYECRAFA LLGWTGSRQF ERDLRRYATH ERKMRLDNHA LYDKTKRVFL   360
KAESEEEIFA HLGLEYIEPL ERNA                                         384

SEQ ID NO: 17             moltype = AA  length = 381
FEATURE                   Location/Qualifiers
REGION                    1..381
                          note = Mouse TdT mutant
source                    1..381
                          mol_type = protein
                          organism = synthetic construct
SEQUENCE: 17
SGSPSPVPGS QNVPAPVVKK ISQYACQRRT TLNNYNQLFT DALDILAEND EFRENEESCL    60
AFRRASSVLK SLPFPITSMK DTEGIPCLGD KVKSIIEGII EDGESSEVKA VLNDERYKSF   120
KLFTSVFGVG LKTAEKWFRM GFRTLSKIQS DKSLRFTQMQ KAGFLYYEDL VSGVNRPEAE   180
AVSMLVKEAV VTFLPDALVT MTGGFRLGKM TGHDVDFLIT SPEATEDEEQ QLLHKVTDFW   240
KQQGLLLYCD ILESTFEKFK QPSRTVDALD HFQKCFLILK LDHPRVHSVK SGQQEGKGWK   300
AIRVDLVMCP YDRRAFALLG WTGSPQFNRD LRRYATHERK MMLDNHALYD KTKRVFLEAE   360
SEEEIFAHLG LDYIEPWERN A                                            381

SEQ ID NO: 18             moltype = AA  length = 381
FEATURE                   Location/Qualifiers
REGION                    1..381
                          note = Mouse TdT mutant
source                    1..381
                          mol_type = protein
                          organism = synthetic construct
SEQUENCE: 18
SGSPSPVPGS QNVPAPVVKK ISQYACQRRT TLNNYNELFT RALDILAEND EFRENEESRD    60
AFRRASSVLK SLPFPITSMK DTEGIPCLGD KVKRIIEEII EDGESSEVKA VLNDERYQAF   120
KLFTSVFGVG RKTAEKWFRM GFRTLEKIRS DKSLRFTQMQ KAGFLYYEDL VSGVNRPEAE   180
AVSMLVKEAV VTFLPDALVT MTGGFRLGKM TGHDVDFLIT SPEATEDEEQ QLLHKVTDFW   240
KQQGLLLYCD ILESTFEKFK QPSRTVDALD HFQKCFLILK LDHPRVHSVK SGQQEGKGWK   300
AIRVDLVMCP YDRRAFALLG WTGSAFFNRD LRRYATHERK MMLDNHALYD KTKRVFLEAE   360
SEEEIFAHLG LDYIEPRERN A                                            381

SEQ ID NO: 19             moltype = AA  length = 381
FEATURE                   Location/Qualifiers
REGION                    1..381
                          note = Mouse TdT mutant
source                    1..381
                          mol_type = protein
                          organism = synthetic construct
SEQUENCE: 19
SGSPSPVPGS QNVPAPVVKK ISQYACQRRT TLNNYNELFT RALDILAEND EFRENEESRD    60
AFRRASSVLK SLPFPITSMK DTEGIPCLGD KVKRIIEEII EDGESSEVKA VLNDERYKAF   120
KLFTSVFGVG RKTAEKWFRM GFRTLEKIRS DKSLRFTQMQ KAGFLYYEDL VSGVNRPEAE   180
AVSMLVKEAV VTFLPDALVT MTGGFRLGKM TGHDVDFLIT SPEATEDEEQ QLLHKVTDFW   240
KQQGLLLYCD ILESTFEKFK QPSRTVDALD HFQKCFLILK LDHPRVHSVK SGQQEGKGWK   300
AIRVDLVMCP YDRRAFALLG WTGSAFFNRD LRRYATHERK MMLDNHALYD KTKRVFLEAE   360
```

```
SEEEIFAHLG LDYIEPWERN A                                                   381

SEQ ID NO: 20           moltype = AA   length = 381
FEATURE                 Location/Qualifiers
REGION                  1..381
                        note = Mouse TdT mutant
source                  1..381
                        mol_type = protein
                        organism = synthetic construct
SEQUENCE: 20
SGSPSPVPGS QNVPAPVVKK ISQYACQRRT TLNNYNELFT RALDILAEND EFRENEESCL          60
AFRRASSVLK SLPFPITSMK DTEGIPCLGD KVKRIIEEII EDGESSEVKA VLNDERYKSF         120
KLFTSVFGVG LKTAEKWFRM GFRTLEKIRS DKSLRFTQMQ KAGFLYYEDL VSGVNRPEAE         180
AVSTLVKEAV VTFLPDALVT MTGGFRLGHM TGHDVDFLIT SPEATEDEEQ QLLHKVTDFW         240
KQQGLLLYCD ILESTFEKFK QPSRKVDALD HFQKCFLILK LDHLRVHSAK SGQQEGKGWK         300
AIRVDLVMCP YDRRAFALLG WTGSVQFKRD LRRYATHERK MMLDEHALYD KTKRVFLEAE         360
SEEEIFAHLG LDYIEPWERN A                                                  381

SEQ ID NO: 21           moltype = DNA  length = 12
FEATURE                 Location/Qualifiers
misc_feature            1..12
                        note = Test Polynucleotide p875
source                  1..12
                        mol_type = other DNA
                        organism = synthetic construct
SEQUENCE: 21
cagttaaaaa ct                                                             12

SEQ ID NO: 22           moltype = DNA  length = 11
FEATURE                 Location/Qualifiers
misc_feature            1..11
                        note = Test Polynucleotide p876
source                  1..11
                        mol_type = other DNA
                        organism = synthetic construct
SEQUENCE: 22
gagttaaaac t                                                              11

SEQ ID NO: 23           moltype = DNA  length = 10
FEATURE                 Location/Qualifiers
misc_feature            1..10
                        note = Test Polynucleotide p877
source                  1..10
                        mol_type = other DNA
                        organism = synthetic construct
SEQUENCE: 23
cagcaaggct                                                                10

SEQ ID NO: 24           moltype = AA   length = 364
FEATURE                 Location/Qualifiers
REGION                  1..364
                        note = TdT(Puma wildtype)
source                  1..364
                        mol_type = protein
                        organism = synthetic construct
SEQUENCE: 24
VVKKIPLYAC QRRTTLNNFN HIFTDAFEVL AENYEFKENE ISSATFMRAA SVLKLPFTII          60
SMKDTEGIPC LGDKVKCVIE EIIEDGESSE VKAVLNDERY QSFKLFTSVF GVGLKTSEKW         120
FRMGFRTLSK IKSDKTLKFT QMQKAGFLYY EDLVSCVTRA EAEAVGVLVK EAVWAFLPDA         180
FVTMTGGFRR GKKIGHDVDF LITIPGSTDE EEEQLLPKVI NLWQRKELLL YYDLVESTFE         240
KLKLPSRKVD ALDHFQKCFL ILKLHHQRVD SGKCSQQEGK TWKAIRVDLV MCPYERRAFA         300
LLGWTGSRQF ERDLRRYATH ERKMILDNHA LYDKTKKIFL KAESEEEIFA HLGLDYIEPW         360
ERNA                                                                     364

SEQ ID NO: 25           moltype = AA   length = 362
FEATURE                 Location/Qualifiers
REGION                  1..362
                        note = wild type N139 reptilian
source                  1..362
                        mol_type = protein
                        organism = synthetic construct
SEQUENCE: 25
YACQRRTTLN NYNKKYTDAF EILAENYEMR ENAGACLAFR RAASVLKFLP FAIVRSNDIE          60
GLPWMGEQVK GIIEDILEEG QSPKVEAVLN NEKYRSFKLF TSVFGVALKT SEKWFMMGLR         120
NLEDVKLNQN LQLTRMQKAG LQHYEDLISY VSKAEADSTS LMVKDTVWKF SPSALVTLTG         180
GFRRGKKMGH DVDFLITVPG SRPNEELLHL VIDCWKKQGL LLYYDLIEST FEKSKLPSQR         240
VDALDHFQKC FAILKLHKER VNQGTSLPPV ASTVEEIKDW KAIRVDLVVS PFEQHAFALL         300
GWTGSRQFER DLRRYATHEK KMMLDNHALY DKTKKIFLSA SSEEEIFAHL GLDYLEPWER         360
NA                                                                       362
```

```
SEQ ID NO: 26              moltype = AA  length = 364
FEATURE                    Location/Qualifiers
REGION                     1..364
                           note = truncated shrew
source                     1..364
                           mol_type = protein
                           organism = synthetic construct
SEQUENCE: 26
VQKISQYACQ RRTTLNNHNH IFTDAFEILA ENCEFRENEG SYVTYMRAAS VLKSLPFSII    60
SMKDTEGIPC LADKVKCVIE EIIEDGESSE VKAVLNDERY KSPKLFTSVF GVGLKTAEKW   120
FRLGFRTLSG IMNDKTLKLT HMQKAGFLYY EDLVSCVTRA EAEAVGVLVK EAVWAFLPDA   180
IVTMTGGFRR GKKVGHDVDF LITSPEATEE QEQQLLHKVI TFWEKEGLLL YCDLYESTFE   240
KLKMPSRKVD ALDHFQKCFL ILKLHRECVD DGTSSQLQGK TWKAIRVDLV VCPYECRAFA   300
LLGWTGSPQF ERDLRRYATH ERKMMLDNHA LYDKTKRKFL SADSEEDIFA HLGLDYIEPW   360
ERNA                                                                364

SEQ ID NO: 27              moltype = AA  length = 369
FEATURE                    Location/Qualifiers
REGION                     1..369
                           note = BOVINE
source                     1..369
                           mol_type = protein
                           organism = synthetic construct
SEQUENCE: 27
KTPPLVVKKI SQYACQRKTT LNNYNEIFTR AFEILAENSE FKENEESYVT FRRAASVLKS    60
LPFTIISMKD TEGIPCLGDK VKRIIEEIIE DGESSEVKAV LNDERYQAFK LFTSVFGVGR   120
KTSEKWFRMG FRSLEKIRSD KTLKFTKMQK AGFLYYEDLV SGVTRAEAEA VGVLVKEAVW   180
AFLPDAFVTM TGGFRLGKKI GHDVDFLITS PGSAEDEEQL LPKVINLWEK KGLLLYYDLV   240
ESTFEKFKLP SRQVDTLDHF QKCFLILKLH HQRVDSSKSN QQEGKTWKAI RVDLVMCPYE   300
NRAFALLGWT GSAFFNRDIR RYATHERKMM LDNHALYDKT KRVFLKAESE EEIFAHLGLD   360
YIEPRERNA                                                           369

SEQ ID NO: 28              moltype = AA  length = 374
FEATURE                    Location/Qualifiers
REGION                     1..374
                           note = LATMERIA
source                     1..374
                           mol_type = protein
                           organism = synthetic construct
SEQUENCE: 28
NVPAPSVVAI SQYACQRRTT LNNHNKIFTD AFEILAENYE FNENEGPCLA FRRAASLLKS    60
LPYAISSMKD LEGLPCLGDQ TKAVIEEILE EGQSSKVQDV LSDERYKSIK LFTSVFGVGL   120
KTAEKWYRKG FRTLEEVQAD KEIKLTKMQK AGFLYYEDIS SAVTKAEAEA IGQIIEDTVR   180
LFAPDAIVTL TGGFRLGKKI GHDVDFLITT PETGNENGLL HKVINVLQNQ GILLYYDIVE   240
STFDKTRLPS RKVDALDHFQ KCFAILKLHK QKVNTSNSEE AEEPSNTETK DWKAIRVDLV   300
ITPFDQYAFA LLGWTGSAFF NRDLRRFATH ERKMMLDNHA LYDKTKKIFL PAKTEEDIFA   360
HLGLDYIEPW ERNA                                                     374

SEQ ID NO: 29              moltype = AA  length = 370
FEATURE                    Location/Qualifiers
REGION                     1..370
                           note = PUMA
source                     1..370
                           mol_type = protein
                           organism = synthetic construct
SEQUENCE: 29
KTESAVVKKI PLYACQRRTT LNNFNEIFTR AFEVLAENYE FKENEISSAT FRRAASVLKS    60
LPFTIISMKD TEGIPCLGDK VKRVIEEIIE DGESSEVKAV LNDERYQAFK LFTSVFGVGL   120
KTSEKWFRMG FRTLEKIKSD KTLKFTQMQK AGFLYYEDLV SGVTRAEAEA VGVLVKEAVW   180
AFLPDAFVTM TGGFRLGKKI GHDVDFLITI PGSTDEEEEQ LLPKVINLWQ RKELLLYYDL   240
VESTFEKLKL PSRKVDALDH FQKCFLILKL HHQRVDSGKC SQQEGKTWKA IRVDLVMCPY   300
ERRAFALLGW TGSAFFNRDL RRYATHERKM ILDNHALYDK TKKIFLKAES EEEIFAHLGL   360
DYIEPWERNA                                                          370

SEQ ID NO: 30              moltype = AA  length = 370
FEATURE                    Location/Qualifiers
REGION                     1..370
                           note = N139
source                     1..370
                           mol_type = protein
                           organism = synthetic construct
SEQUENCE: 30
KTESAVVKKI PLYACQRRTT LNNFNEIFTR AFEVLAENYE FKENEISSAT FRRAASVLKS    60
LPFTIISMKD TEGIPCLGDK VKRVIEEIIE DGESSEVKAV LNDERYQAFK LFTSVFGVGL   120
KTSEKWFRMG FRTLEKIKSD KTLKFTQMQK AGFLYYEDLV SGVTRAEAEA VGVLVKEAVW   180
AFLPDAFVTM TGGFRLGKKI GHDVDFLITI PGSTDEEEEQ LLPKVINLWQ RKELLLYYDL   240
VESTFEKLKL PSRKVDALDH FQKCFLILKL HHQRVDSGKC SQQEGKTWKA IRVDLVMCPY   300
ERRAFALLGW TGSAFFNRDL RRYATHERKM ILDNHALYDK TKKIFLKAES EEEIFAHLGL   360
```

```
DYIEPWERNA                                                                     370

SEQ ID NO: 31           moltype = AA  length = 370
FEATURE                 Location/Qualifiers
REGION                  1..370
                        note = SHREW
source                  1..370
                        mol_type = protein
                        organism = synthetic construct
SEQUENCE: 31
NVPAPVVQKI SQYACQRRTT LNNHNHIFTD AFEILAENDE FRENEESRDA FRRAASVLKS    60
LPFSIISMKD TEGIPCLADK VKRVIEEIIE DGESSEVKAV LNDERYKAFK LFTSVFGVGR   120
KTAEKWFRLG FRTLEGIRND KTLKLTHMQK AGFLYYEDLV SGVTRAEAEA VGVLVKEAVW   180
AFLPDAIVTM TGGFRLGKKV GHDVDFLITS PEATEEQEQQ LLHKVITFWE KEGLLLYCDL   240
YESTFEKLKM PSRTVDALDH FQKCFLILKL HRESVDDGTS SQLQGKTWKA IRVDLVVCPY   300
ECRAFALLGW TGSPFFNRDL RRYATHERKM MLDNHALYDK TKRKFLSADS EEDIFAHLGL   360
DYIEPRERNA                                                         370

SEQ ID NO: 32           moltype = AA  length = 381
FEATURE                 Location/Qualifiers
REGION                  1..381
                        note = M27
source                  1..381
                        mol_type = protein
                        organism = synthetic construct
SEQUENCE: 32
NSSPSPVPGS QNVPAPVVKK ISQYACQRRT TLNNYNQLFT DALDILAEND EFRENEESCL    60
AFRRASSVLK SLPFPITSMK DTEGIPCLGD KVKSIIEGII EDGESSEVKA VLNDERYKSF   120
KLFTSVFGVG LKTAEKWFRM GFRTLSKIQS DKSLRFTQMQ KAGFLYYEDL VSGVNRPEAE   180
AVSMLVKEAV VTFLPDALVT MTGGFRLGKM TGHDVDFLIT SPEATEDEEQ QLLHKVTDFW   240
KQQGLLLYCD ILESTFEKFK QPSRTVDALD HFQKCFLILK LDHPRVHSVK SGQQEGKGWK   300
AIRVDLVMCP YDRRAFALLG WTGSPQFNRD LRRYATHERK MMLDNHALYD KTKRVFLEAE   360
SEEEIFAHLG LDYIEPWERN A                                             381

SEQ ID NO: 33           moltype = DNA  length = 20
FEATURE                 Location/Qualifiers
misc_feature            1..20
                        note = PRIMER
source                  1..20
                        mol_type = other DNA
                        organism = synthetic construct
SEQUENCE: 33
taatacgact cactataggg                                                20

SEQ ID NO: 34           moltype = DNA  length = 19
FEATURE                 Location/Qualifiers
misc_feature            1..19
                        note = PRIMER
source                  1..19
                        mol_type = other DNA
                        organism = synthetic construct
SEQUENCE: 34
gctagttatt gctcagcgg                                                 19
```